(12) United States Patent
Long et al.

(10) Patent No.: US 7,902,221 B2
(45) Date of Patent: Mar. 8, 2011

(54) AMIDOALKYL-8-AZABICYCLO[3.2.1]OCTANE COMPOUNDS AS MU OPIOID RECEPTOR ANTAGONISTS

(75) Inventors: Daniel D. Long, San Francisco, CA (US); Daisuke Roland Saito, Burlingame, CA (US); Priscilla Van Dyke, San Francisco, CA (US); Lan Jiang, Foster City, CA (US); Tmothy J. Church, San Mateo, CA (US); John R. Jacobsen, San Mateo, CA (US)

(73) Assignee: Theravance, Inc., South San Francisco, CA (US)

( * ) Notice: Subject to any disclaimer, the term of this patent is extended or adjusted under 35 U.S.C. 154(b) by 276 days.

(21) Appl. No.: 12/229,748

(22) Filed: Aug. 26, 2008

(65) Prior Publication Data

US 2009/0062335 A1 Mar. 5, 2009

Related U.S. Application Data

(60) Provisional application No. 60/966,282, filed on Aug. 27, 2007.

(51) Int. Cl.
A61K 31/46 (2006.01)
C07D 221/02 (2006.01)
A61P 1/00 (2006.01)
(52) U.S. Cl. ........................ 514/304; 546/124
(58) Field of Classification Search .................. 546/124; 514/304
See application file for complete search history.

(56) References Cited

U.S. PATENT DOCUMENTS

| | | | |
|---|---|---|---|
| 5,159,081 A | 10/1992 | Cantrell et al. | |
| 6,313,312 B1 | 11/2001 | Banks et al. | |
| 6,469,030 B2 | 10/2002 | Farrar et al. | |
| 6,479,516 B1 | 11/2002 | Gibson et al. | |
| 6,593,348 B2 | 7/2003 | Carroll et al. | |
| 6,610,711 B2 | 8/2003 | Armer et al. | |
| 6,992,090 B2 | 1/2006 | Le Bourdonnec et al. | |
| 7,049,335 B2 | 5/2006 | McHardy et al. | |
| 7,056,930 B2 | 6/2006 | Coe et al. | |
| 7,087,749 B2 | 8/2006 | Dolle et al. | |
| 7,241,887 B2 | 7/2007 | Coe et al. | |
| 2002/0025948 A1 | 2/2002 | Banks et al. | |
| 2003/0181447 A1 | 9/2003 | Boyd et al. | |
| 2004/0186135 A1 | 9/2004 | Dolle et al. | |
| 2004/0204453 A1 | 10/2004 | McHardy et al. | |
| 2007/0105863 A1 | 5/2007 | Dolle et al. | |
| 2007/0219278 A1 | 9/2007 | Long et al. | |
| 2008/0207676 A1 | 8/2008 | Dalziel et al. | |
| 2009/0023934 A1 | 1/2009 | Colson et al. | |
| 2009/0062332 A1 | 3/2009 | Saito et al. | |
| 2009/0062333 A1 | 3/2009 | Saito et al. | |
| 2009/0062334 A1 | 3/2009 | Long et al. | |

FOREIGN PATENT DOCUMENTS

| | | | |
|---|---|---|---|
| WO | 2004089908 | * | 10/2004 |
| WO | WO 2004/089908 A2 | | 10/2004 |
| WO | WO 2004/089909 A1 | | 10/2004 |
| WO | WO 2004/092165 A1 | | 10/2004 |

OTHER PUBLICATIONS

Cha et al., "Rhodamine-Labeled 2beta-carbomethoxy-3beta-(3,4-dichlorophenyl)tropane Analogues as High-Affinity Fluorescent Probes for the Dopamine Transporter", Journal of Medicinal Chemistry, vol. 48, No. 24, pp. 7513-7516 (2005).
Le Bourdonnec et al., "*trans*-3,4-Dimethyl-4-(3-carboxamidophenyl)piperidines: A Novel Class of µ-Selective Opioid Antagonists", Bioorganic & Medicinal Chemistry Letters, vol. 13 pp. 4459-4462 (2003).
Le Bourdonnec et al., "Elucidation of the Bioactive Conformation of the N-Substituted *trans*-3,4-Dimethyl-4-(3-hydroxyphenyl)piperidine Class of µ-Opioid Receptor Antagonists", Journal of Medicinal Chemistry, vol. 49, pp. 7278-7289 (2006).
Le Bourdonnec et al., "Synthesis and Pharmacological Evaluation of Novel Octahydro-1H-pyrido[1,2-a]pyrazine as µ-Opioid Receptor Antagonists", Journal of Medicinal Chemistry, vol. 49, pp. 7290-7306 (2006).
Diaz et al., "SAR and Biological Evaluation of Novel *trans*-3,4-dimethyl-4-arylpiperidine Derivatives as Opioid Antagonists", Bioorganic & Medicinal Chemistry Letters, vol. 15 pp. 3844-3848 (2005).
Lu et al., "Substituted Bridged Phenyl Piperidines: Orally Active Growth Hormone Secretagogues", Bioorganic & Medicinal Chemistry Letters, 13, pp. 1817-1820 (2003).
International Search Report for PCT/US2008/010090 (3 pages).

* cited by examiner

*Primary Examiner* — D. Margaret Seaman
*Assistant Examiner* — Niloofar Rahmani
(74) *Attorney, Agent, or Firm* — Jeffrey A. Hagenah; Roberta P. Saxon

(57) ABSTRACT

The invention provides novel 8-azabicyclo[3.2.1]octane compounds of formula (I):

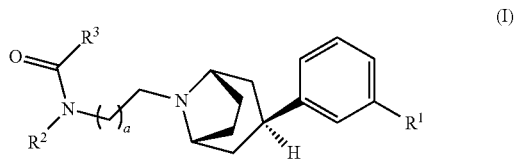

wherein $R^1$, $R^2$, $R^3$, and a are defined in the specification, or a pharmaceutically-acceptable salt thereof, that are antagonists at the mu opioid receptor. The invention also provides pharmaceutical compositions comprising such compounds, methods of using such compounds to treat conditions associated with mu opioid receptor activity, and processes and intermediates useful for preparing such compounds.

14 Claims, No Drawings

AMIDOALKYL-8-AZABICYCLO[3.2.1]OCTANE COMPOUNDS AS MU OPIOID RECEPTOR ANTAGONISTS

CROSS-REFERENCE TO RELATED APPLICATIONS

This application claims the benefit of U.S. Provisional Application No. 60/966,282, filed on Aug. 27, 2007, the disclosure of which is incorporated herein by reference in its entirety.

BACKGROUND OF THE INVENTION

1. Field of the Invention

The invention is directed to 8-azabicyclo[3.2.1]octane compounds which are useful as mu opioid receptor antagonists. The invention is also directed to pharmaceutical compositions comprising such compounds, methods of using such compounds for treating or ameliorating medical conditions mediated by mu opioid receptor activity, and processes and intermediates useful for preparing such compounds.

2. State of the Art

It is now generally understood that endogenous opioids play a complex role in gastrointestinal physiology. Opioid receptors are expressed throughout the body, both in the central nervous system and in peripheral regions including the gastrointestinal (GI) tract.

Compounds which function as agonists at opioid receptors, of which morphine is a prototypical example, are the mainstays of analgesic therapy for the treatment of moderate to severe pain. Unfortunately, use of opioid analgesics is often associated with adverse effects on the GI tract, collectively termed opioid-induced bowel dysfunction (OBD). OBD includes symptoms such as constipation, decreased gastric emptying, abdominal pain and discomfort, bloating, nausea, and gastroesophageal reflux. Both central and peripheral opioid receptors are likely involved in the slowdown of gastrointestinal transit after opioid use. However, evidence suggests that peripheral opioid receptors in the GI tract are primarily responsible for the adverse effects of opioids on GI function.

Since the side effects of opioids are predominantly mediated by peripheral receptors, whereas the analgesia is central in origin, a peripherally selective antagonist can potentially block undesirable GI-related side effects without interfering with the beneficial central effects of analgesia or precipitating central nervous system withdrawal symptoms.

Of the three major opioid receptor subtypes, denoted mu, delta, and kappa, most clinically-used opioid analgesics are thought to act via mu opioid receptor activation to exert analgesia and to alter GI motility. Accordingly, peripherally selective mu opioid antagonists are expected to be useful for treating opioid-induced bowel dysfunction. Preferred agents will demonstrate significant binding to mu opioid receptors in vitro and be active in vivo in GI animal models.

Postoperative ileus (POI) is a disorder of reduced motility of the GI tract that occurs after abdominal or other surgery. The symptoms of POI are similar to those of OBD. Furthermore, since surgical patients are often treated during and after surgery with opioid analgesics, the duration of POI may be compounded by the reduced GI motility associated with opioid use. Mu opioid antagonists useful for treating OBD are therefore also expected to be beneficial in the treatment of POI.

SUMMARY OF THE INVENTION

The invention provides novel compounds that possess mu opioid receptor antagonist activity.

Accordingly, the invention provides a compound of formula (I):

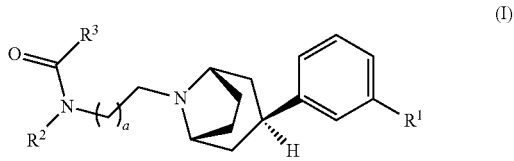

wherein:
$R^1$ is —$OR^a$ or —$C(O)NR^bR^c$;
$R^2$ is $C_{4-10}$ alkyl or $C_{4-10}$ alkenyl;
$R^3$ is $C_{1-6}$ alkyl substituted with one or two substituents selected from —$OR^d$, —$S(O)_2R^e$, —$NR^fR^g$, and —$C(O)R^4$;
$R^4$ is $C_{1-3}$alkyl, optionally substituted with one —$OR^d$ or —$S(O)_2R^e$;
$R^a$, $R^b$, $R^c$, $R^d$, $R^f$, and $R^g$ are each independently hydrogen or $C_{1-3}$alkyl;
$R^e$ is $C_{1-3}$alkyl; and
a is 1, 2, 3, 4, or 5;
or a pharmaceutically-acceptable salt thereof.

The invention also provides a pharmaceutical composition comprising a compound of the invention and a pharmaceutically-acceptable carrier.

The invention also provides a method of treating a disease or condition ameliorated by treatment with a mu opioid receptor antagonist, e.g. a disorder of reduced motility of the gastrointestinal tract such as opioid-induced bowel dysfunction and post-operative ileus, the method comprising administering to the mammal, a therapeutically effective amount of a compound or of a pharmaceutical composition of the invention.

The compounds of the invention can also be used as research tools, i.e. to study biological systems or samples, or for studying the activity of other chemical compounds. Accordingly, in another of its method aspects, the invention provides a method of using a compound of formula (I), or a pharmaceutically acceptable salt thereof, as a research tool for studying a biological system or sample or for discovering new compounds having mu opioid receptor activity, the method comprising contacting a biological system or sample with a compound of the invention and determining the effects caused by the compound on the biological system or sample.

In separate and distinct aspects, the invention also provides synthetic processes and intermediates described herein, which are useful for preparing compounds of the invention.

The invention also provides a compound of the invention as described herein for use in medical therapy, as well as the use of a compound of the invention in the manufacture of a formulation or medicament for treating a disease or condition ameliorated by treatment with a mu opioid receptor antagonist, e.g. a disorder of reduced motility of the gastrointestinal tract, in a mammal.

DETAILED DESCRIPTION OF THE INVENTION

The invention provides 8-azabicyclo[3.2.1]octane mu opioid receptor antagonists of formula (I), or pharmaceutically-acceptable salts thereof. The following substituents and values are intended to provide representative examples of various aspects of this invention. These representative values are intended to further define such aspects and are not intended to exclude other values or limit the scope of the invention.

In a specific aspect of the invention, $R^1$ is —$OR^a$ or —$C(O)NR^bR^c$.

In another specific aspect, $R^1$ is —OH or —$C(O)NH_2$.

In yet another specific aspect, $R^1$ is —$C(O)NH_2$.

In a specific aspect, $R^2$ is $C_{4-10}$alkyl or $C_{4-10}$alkenyl;

In another specific aspect, $R^2$ is $C_{4-10}$alkyl.

In another specific aspect, $R^2$ is a branched $C_{5-8}$alkyl. Representative $R^2$ groups within this aspect include, but are not limited to, 2,2-dimethylpropyl, 2-methylbutyl, 3-methylbutyl, 2-ethylbutyl, 2,2-dimethylpentyl, and 2-propylpentyl.

In yet another specific aspect, $R^2$ is 2-ethylbutyl.

In a specific aspect, $R^3$ is $C_{1-6}$ alkyl substituted with one or two substituents selected from —$OR^d$, —$S(O)_2R^e$, —$NR^fR^g$, and —$C(O)R^4$.

In another specific aspect, $R^3$ is $C_{1-6}$alkyl substituted with one or two substituents selected from —$OR^d$, —$S(O)_2R^e$, and —$NR^fR^g$.

In another specific aspect $R^3$ is $C_{1-4}$alkyl substituted with one or two substituents selected from —OH, —$SO_2CH_3$, and —$NH_2$.

In yet another specific aspect $R^3$ is $C_{1-4}$alkyl substituted with one or two substituents selected from —OH and —$SO_2CH_3$. Representative $R^3$ groups within this aspect include, but are not limited to, hydroxymethyl, 1-hydroxyethyl, methanesulfonylmethyl, 1,2-dihydroxyethyl, 1,1-dimethyl-2-hydroxyethyl, 1-methanesulfonyl-1-methylethyl, 1,2-dihydroxypropyl, 1-methyl-1-hydroxymethyl-2-hydroxyethyl, 1-hydroxy-3-dimethylaminopropyl, and 1-hydroxy-2-dimethylaminoethyl.

In a specific aspect, $R^a$, $R^b$, $R^c$, $R^d$, $R^f$, and $R^g$ are each independently hydrogen or $C_{1-3}$alkyl.

In another specific aspect, $R^a$, $R^b$, $R^c$, $R^d$, $R^f$, and $R^g$ are each independently hydrogen or methyl.

In another specific aspect, $R^a$, $R^b$, $R^c$, and $R^d$ are each hydrogen.

In another specific aspect, $R^f$ and $R^g$ are each methyl.

In a specific aspect, $R^e$ is $C_{1-3}$alkyl.

In another specific aspect, $R^e$ is methyl.

In a specific aspect, a is 1, 2, 3, 4, or 5.

In another specific aspect, a is 1 or 2.

In yet other specific aspects, a is 1; or a is 2.

In a specific aspect, the invention provides a compound of formula (I) wherein:
$R^1$ is —$C(O)NH_2$;
$R^2$ is a branched $C_{5-8}$alkyl;
$R^3$ is $C_{1-4}$ alkyl substituted with one or two substituents selected from —OH and —$SO_2CH_3$;
a is 1 or 2;
or a pharmaceutically-acceptable salt thereof.

The invention further provides the compounds of Examples 1 to 45 herein.

The chemical naming convention used herein is illustrated for the compound of Example 1

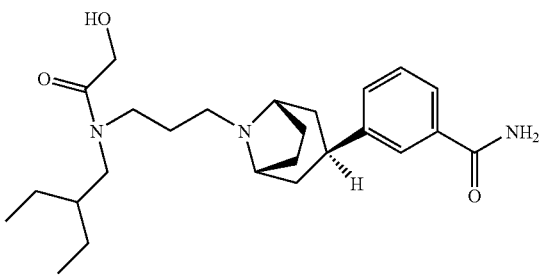

which is 3-endo-(8-{3-[(2-ethylbutyl)-(2-hydroxyacetyl)amino]propyl}-8-aza-bicyclo[3.2.1]oct-3-yl)-benzamide. Alternatively, using the IUPAC conventions as implemented in AutoNom software, (MDL Information Systems, GmbH, Frankfurt, Germany), the compound is denoted 3-((1R,3R,5S)-8-{3-[(2-ethylbutyl)-(2-hydroxy-acetyl)amino]propyl}-8-azabicyclo[3.2.1]oct-3-yl)benzamide. The names used herein therefore correspond to the IUPAC notation with the endo orientation of the substituted phenyl group with respect to the 8-azabicyclo[3.2.1]octane group indicated explicitly. All of the compounds of the invention are in the endo orientation. For convenience, as used herein, the term "8-azabicyclooctane" means 8-azabicyclo[3.2.1]octane.

In addition to the endo stereochemistry with respect to the bicyclo group, the compounds of the invention may contain a chiral center in the substituents $R^2$ and $R^3$. Accordingly, the invention includes racemic mixtures, pure stereoisomers, and stereoisomer-enriched mixtures of such isomers, unless otherwise indicated. When the stereochemistry of a compound is specified, including both the orientation with respect to the 8-azabicyclooctane group and the chirality in a substituent $R^2$ or $R^3$, it will be understood by those skilled in the art, that minor amounts of other stereoisomers may be present in the compositions of the invention unless otherwise indicated, provided that any utility of the composition as a whole is not eliminated by the presence of such other isomers.

Definitions

When describing the compounds, compositions and methods of the invention, the following terms have the following meanings, unless otherwise indicated.

The term "alkyl" means a monovalent saturated hydrocarbon group which may be linear or branched or combinations thereof. Unless otherwise defined, such alkyl groups typically contain from 1 to 10 carbon atoms. Representative alkyl groups include, by way of example, methyl, ethyl, n-propyl (n-Pr), isopropyl (i-Pr), n-butyl (n-Bu), sec-butyl, isobutyl, tert-butyl, n-pentyl, n-hexyl, 2,2-dimethylpropyl, 2-methylbutyl, 3-methylbutyl, 2-ethylbutyl, 2,2-dimethylpentyl, 2-propylpentyl, and the like.

The term "alkylenyl" means a divalent saturated hydrocarbon group which may be linear or branched or combinations thereof. Unless otherwise defined, such alkylenyl groups typically contain from 1 to 10 carbon atoms. Representative alkylenyl groups include, by way of example, methylene, ethylene, n-propylene, n-butylene, propane-1,2-diyl (1-methylethylene), 2-methylpropane-1,2-diyl (1,1-dimethylethylene) and the like.

The term "compound" means a compound that was synthetically prepared or prepared in any other way, such as by in vivo metabolism.

The term "therapeutically effective amount" means an amount sufficient to effect treatment when administered to a patient in need of treatment.

The term "treatment" as used herein means the treatment of a disease, disorder, or medical condition in a patient, such as a mammal (particularly a human) which includes:
(a) preventing the disease, disorder, or medical condition from occurring, i.e., prophylactic treatment of a patient;
(b) ameliorating the disease, disorder, or medical condition, i.e., eliminating or causing regression of the disease, disorder, or medical condition in a patient, including counteracting the effects of other therapeutic agents;
(c) suppressing the disease, disorder, or medical condition, i.e., slowing or arresting the development of the disease, disorder, or medical condition in a patient; or
(d) alleviating the symptoms of the disease, disorder, or medical condition in a patient.

The term "pharmaceutically-acceptable salt" means a salt prepared from an acid or base which is acceptable for administration to a patient, such as a mammal. Such salts can be derived from pharmaceutically-acceptable inorganic or organic acids and from pharmaceutically-acceptable bases. Typically, pharmaceutically-acceptable salts of compounds of the present invention are prepared from acids.

Salts derived from pharmaceutically-acceptable acids include, but are not limited to, acetic, adipic, benzenesulfonic, benzoic, camphorsulfonic, citric, ethanesulfonic, fumaric, gluconic, glutamic, glycolic, hydrobromic, hydrochloric, lactic, maleic, malic, mandelic, methanesulfonic, mucic, nitric, oxalic, pantothenic, phosphoric, succinic, sulfuric, tartaric, p-toluenesulfonic, xinafoic (1-hydroxy-2-naphthoic acid), naphthalene-1,5-disulfonic acid and the like.

The term "amino-protecting group" means a protecting group suitable for preventing undesired reactions at an amino nitrogen. Representative amino-protecting groups include, but are not limited to, formyl; acyl groups, for example alkanoyl groups, such as acetyl and trifluoroacetyl; alkoxycarbonyl groups, such as tert-butoxycarbonyl (Boc); arylmethoxycarbonyl groups, such as benzyloxycarbonyl (Cbz) and 9-fluorenylmethoxycarbonyl (Fmoc); arylmethyl groups, such as benzyl (Bn), trityl (Tr), and 1,1-di-(4'-methoxyphenyl)methyl; silyl groups, such as trimethylsilyl (TMS) and tert-butyldimethylsilyl (TBDMS); and the like.

General Synthetic Procedures

Compounds of the invention can be prepared from readily available starting materials using the following general methods and procedures. Although a particular aspect of the present invention is illustrated in the schemes below, those skilled in the art will recognize that all aspects of the present invention can be prepared using the methods described herein or by using other methods, reagents and starting materials known to those skilled in the art. It will also be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group, as well as suitable conditions for protection and deprotection, are well known in the art. For example, numerous protecting groups, and their introduction and removal, are described in T. W. Greene and G. M. Wuts, *Protecting Groups in Organic Synthesis*, Third Edition, Wiley, New York, 1999, and references cited therein.

In one method of synthesis, compounds of the invention are prepared as illustrated in Scheme A. (The substituents and variables shown in the following schemes have the definitions provided above unless otherwise indicated).

Scheme A

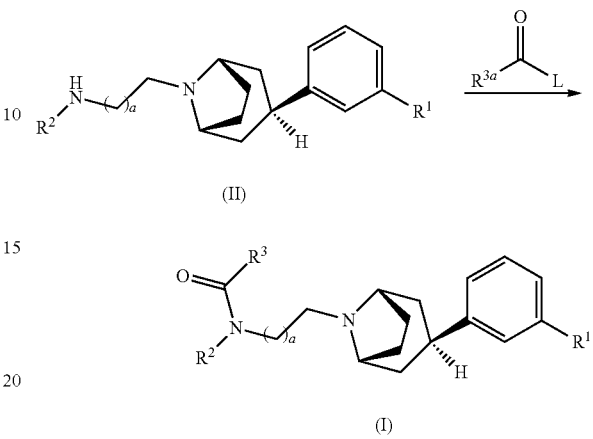

In Scheme A, $R^{3a}$ represents $R^3$ or a protected form of $R^3$, and L represents a leaving group, such as chloro, or $R^{3a}C(O)$-L represents a carboxylic acid or a carboxylate salt. For example, to prepare a compound in which $R^3$ is —$CH_2OH$, a useful reagent is acetoxyacetyl chloride, in which $R^{3a}$ is —$CH_2OC(O)CH_3$ and L is chloro. When $R^{3a}$ is a protected form of $R^3$, the reaction also includes a deprotection step, which is not shown.

Optimal reaction conditions for the reaction of Scheme A may vary depending on the chemical properties of the reagent $R^{3a}C(O)$-L, as is well known to those skilled in the art. For example, when L is a halo leaving group, such as chloro, the reaction is typically conducted by contacting intermediate (II) with between about 1 and about 2 equivalents of a compound of formula $R^{3a}C(O)$-L in an inert diluent, such as dichloromethane. Optionally, the reaction is conducted in the presence of an excess of base, for example between about 3 and about 6 equivalents of base, such as N,N-diisopropylethylamine or triethylamine. Suitable inert diluents also include 1,1,2,2-tetrachloroethane, tetrahydrofuran, dimethylacetamide, and the like. The reaction is typically conducted at a temperature in the range of about −50° C. to about 30° C. for about a quarter hour to about 16 hours, or until the reaction is substantially complete.

When the reagent $R^{3a}C(O)$-L is a carboxylic acid or a carboxylate salt, the reaction is typically conducted by contacting intermediate (II) with between about 1 and about 5 equivalents of the acid $R^{3a}C(O)OH$ or the carboxylate salt, for example, $R^{3a}C(O)OLi$, in an inert diluent, optionally in the presence of an excess of base, both as described above, and in the presence of between about 1 and about 6 equivalents of an activating agent such as N,N-carbonyl diimidazole (CDI), N,N,N',N'-tetramethyl-O-(7-azabenzotriazol-1-yl)uronium hexafluorophosphate (HATU) or 1-(3-dimethylaminopropyl)-3-ethylcarbodiimide (EDC). The reaction is typically conducted at a temperature in the range of about 25° C. to about 100° C. for about 2 hours to about 16 hours, or until the reaction is substantially complete.

General procedures for the preparation of an intermediate of formula (II) are illustrated in Scheme B1

Scheme B1

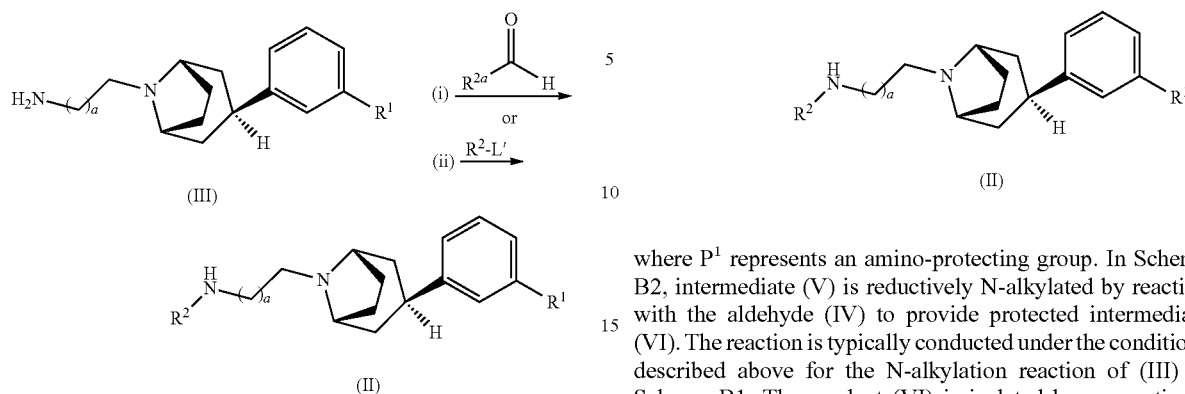

where $R^{2a}$ is defined such that $R^{2a}$—$CH_2$— is $R^2$ and L' is a leaving group such as chloro or bromo.

In reaction (i), an intermediate of formula (III), is reductively N-alkylated by reaction with an aldehyde of formula $R^{2a}C(O)H$ to provide intermediate (II). The reaction is typically conducted by contacting intermediate (III) with between about 1 and about 2 equivalents of an aldehyde of formula $R^{2a}C(O)H$ in a suitable inert diluent, such as dichloromethane, in the presence of between about 0.9 and about 2 equivalents of a reducing agent. The reaction is typically conducted at a temperature in the range of about 0° C. to ambient temperature for about a half hour to about 3 hours or until the reaction is substantially complete. Typical reducing agents include sodium triacetoxyborohydride, sodium borohydride, and sodium cyanoborohydride. The product (II) is isolated by conventional means.

Alternatively, intermediate (II) is prepared by reaction of (III) with an alkyl halide of the formula $R^2$-L' as shown in reaction (ii). The reaction is typically conducted by contacting intermediate (III) with between about 1 and about 2 equivalents of alkyl halide $R^2$-L' in an inert diluent, such as dimethylsulfoxide, or the like. The reaction is typically conducted at a temperature in the range of about 25° C. to about 80° C. for about a half hour to about 16 hours or until the reaction is substantially complete.

Another general procedure for the preparation of an intermediate of formula (II) is illustrated in Scheme B2.

Scheme B2

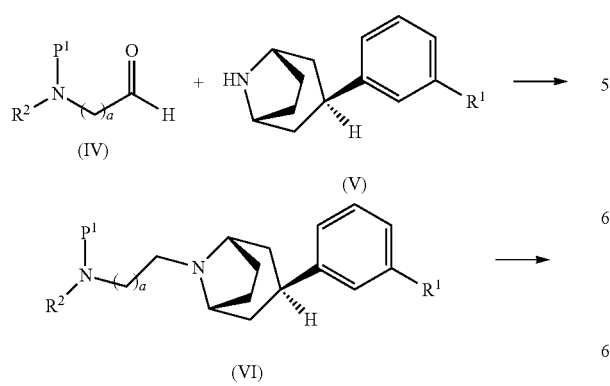

where $P^1$ represents an amino-protecting group. In Scheme B2, intermediate (V) is reductively N-alkylated by reaction with the aldehyde (IV) to provide protected intermediate (VI). The reaction is typically conducted under the conditions described above for the N-alkylation reaction of (III) in Scheme B1. The product (VI) is isolated by conventional procedures. The deprotection of (VI) uses standard procedures. For example, when the protecting group $P^1$ is Boc, (VI) is typically treated with an acid, such as trifluoroacetic acid to provide intermediate (II).

Intermediates of formula (III) can be prepared by reactions analogous to those shown in Scheme B2 using the aldehyde (VII):

in place of aldehyde (IV).

Intermediates of formula (IV) can be prepared as illustrated in Scheme C:

Scheme C

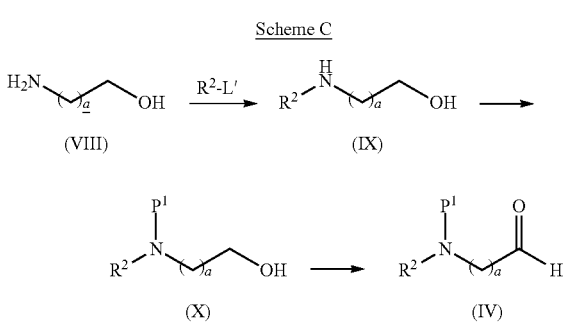

where all the variables take the values defined above. First, alcohol (IX) is prepared by reaction of an alcohol of formula (VIII) with an alkyl halide $R^2$-L' under conditions similar to those of Scheme B1, reaction (ii). Next, addition of an amino-protecting group by conventional procedures forms intermediate (X), which is oxidized to provide an intermediate of formula (IV).

Intermediates of formula (V) can be prepared from readily available starting materials. For example, one process for the preparation of intermediate (V') in which $R^1$ is hydroxy is illustrated in Scheme D.

Scheme D

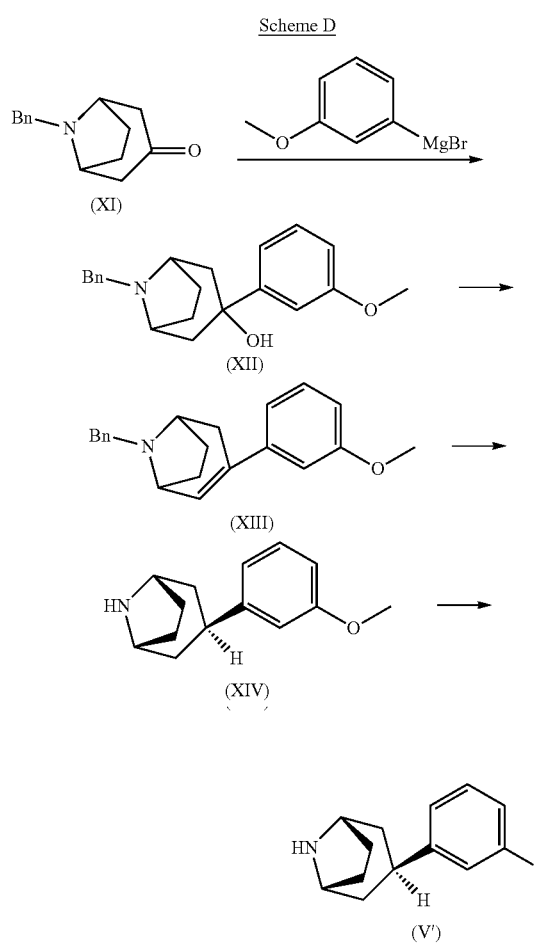

where Bn denotes the amino-protecting group benzyl. Protected 8-azabicyclo[3.2.1]octanone (XI) is typically obtained from commercial sources and it can be prepared by the reaction of 2,5-dimethoxytetrahydrofuran with benzylamine and 1,3-acetonedicarboxylic acid in an acidic aqueous solution in the presence of a buffering agent as described in US 2005/0228014. (See also, U.S. Pat. No. 5,753,673).

First, intermediate (XI) is added to a solution of between about 1 and about 2 equivalents of the Grignard reagent 3-methoxyphenyl magnesium bromide in an inert diluent. The reaction is typically conducted at a temperature of between about 0° C. and about 10° C. for between about 1 and about 3 hours or until the reaction is substantially complete. Transmetalation of the Grignard reagent from magnesium to cerium by reaction with an equivalent amount of cerous chloride prior to use is advantageous for obtaining a good yield of intermediate (XII). The hydroxy substituent is eliminated from intermediate (XII) by treatment with aqueous 6N HCl to provide the hydrochloride salt of intermediate (XIII). This reaction is typically conducted at a temperature of between about 50° C. and about 100° C. for between about 1 and about 3 hours or until the reaction is substantially complete.

Hydrogenation of intermediate (XIII) saturates the double bond of the alkene moiety and removes the benzyl protecting group to provide intermediate (XIV). Typically, the reaction is conducted by exposing the HCl salt of (XIII) dissolved in ethanol to a hydrogen atmosphere in the presence of a transition metal catalyst. Finally, the methyl group is removed from intermediate (XIV) by contacting a cooled solution of intermediate (XIV) in an inert diluent with between about 1 and about 2 equivalents of boron tribromide, hydrogen bromide, or boron trichloride. The reaction is typically conducted at a temperature of between about −80° C. and about 0° C. for between about 12 and about 36 hours or until the reaction is substantially complete. Intermediate (V') can be isolated by conventional procedures as a free base or as a hydrobromide salt. Crystallization of the hydrobromide salt provides intermediate (V') with high stereospecificity in the endo configuration (endo to exo ratio of greater than 99.1:0.8).

A process for preparing intermediate (V″) in which the variable $R^1$ is —C(O)NH$_2$ uses the phenol intermediate (V') as a starting material as shown in Scheme E.

Scheme E

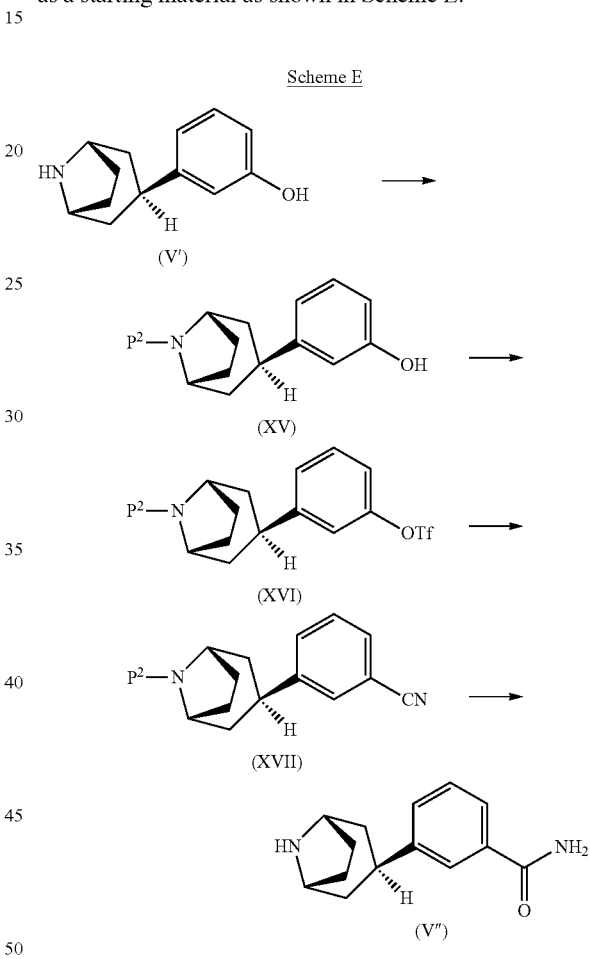

where —OTf represents trifluoromethane sulfonate (commonly triflate) and $P^2$ represents an amino-protecting group, such as Boc or trifluoroacetyl.

For example, when Boc is used as the protecting group, first, the phenol intermediate (V') is typically reacted with about 1 equivalent of di-tert-butyl dicarbonate (commonly Boc$_2$O) to provide the Boc-protected intermediate (XV). The reactants are typically cooled to about 0° C. and then allowed to warm to ambient temperature over a period of between about 12 and about 24 hours. When trifluoroacetyl is used as the protecting group, typically (V') is reacted with about 2 equivalents of trifluoroacetyl anhydride to form the protected intermediate (XV). Next, intermediate (XV) in an inert diluent is contacted with a slight excess, for example about 1.1 equivalents of trifluoromethane sulfonyl chloride in the presence of between about 1 and about 2 equivalents of base to provide intermediate (XVI), which can be isolated by conventional procedures. Reaction of (XVI) with zinc cyanide in the presence of a transition metal catalyst, provides intermediate (XVII). This reaction is typically conducted at a temperature between about 60° C. and 120° C. under an inert atmosphere for about 2 to about 12 hours or until the reaction is substantially complete.

Finally, the nitrile intermediate (XVII) is hydrolyzed and deprotected to provide the carboxamide intermediate (V"). Typically, in this reaction, when $P^2$ is Boc, intermediate (XVII) in an acidic solvent, for example trifluoroacetic acid, is contacted with between about 4 and about 6 equivalents of concentrated sulfuric acid. Typically the reaction is conducted in the temperature range of between about 50° C. and about 80° C. for about 8 to about 24 hours or until the reaction is substantially complete. The product is typically isolated in freebase form. When a trifluoroacetyl protecting group is used, the nitrile intermediate is first hydrolyzed to the carboxamide in concentrated sulfuric acid as described above. Quenching of the hydrolysis reaction by addition of base also removes the protecting group. The product is typically isolated as the hydrochloric acid salt.

In an alternate process for the preparation of compounds of the invention of formula (I), intermediate (V) is reacted with an intermediate of formula (XVIII)

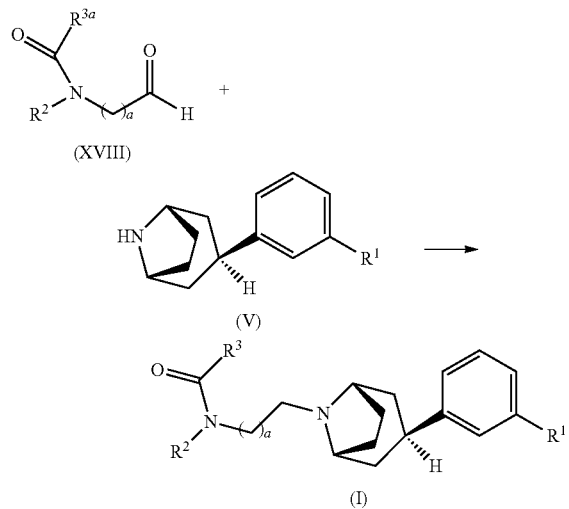

Scheme F under conditions similar to those described for the initial reaction of Scheme B2. When $R^{3a}$ is a protected form of $R^3$, a final deprotection step is performed to provide compound (I). Intermediate (XVIII) can be prepared by reaction of the alcohol (IX) with the reagent $R^{3a}C(O)$-L to add —$C(O)R^{3a}$ to the nitrogen of (IX), followed by oxidation of the resulting alcohol to the aldehyde (XVIII).

Further details regarding specific reaction conditions and other procedures for preparing representative compounds of the invention or intermediates thereto are described in the examples below.

Accordingly, in a method aspect, the invention provides a process for preparing a compound of formula (I), or a salt or protected derivative thereof, the process comprising (a) reacting a compound of formula (II) with a compound of formula $R^{3a}C(O)$-L, or (b) reacting a compound of formula (V) with a compound of formula (XVIII); and optionally, removing the protecting group or groups from $R^{3a}$, to provide a compound of formula (I) or a salt or protected derivative thereof.

In an additional aspect, the invention provides a compound of formula (II), wherein the variables $R^1$, $R^2$ and a take any of the values described in aspects of the invention disclosed above. In particular, the invention provides a compound of formula (II), wherein $R^1$ is —$C(O)NH_2$, $R^2$ is a branched $C_{5-8}$alkyl, and a is 1 or 2.

Pharmaceutical Compositions

The 8-azabicyclooctane compounds of the invention are typically administered to a patient in the form of a pharmaceutical composition or formulation. Such pharmaceutical compositions may be administered to the patient by any acceptable route of administration including, but not limited to, oral, rectal, vaginal, nasal, inhaled, topical (including transdermal) and parenteral modes of administration.

Accordingly, in one of its compositions aspects, the invention is directed to a pharmaceutical composition comprising a pharmaceutically-acceptable carrier or excipient and a therapeutically effective amount of a compound of formula (I) or a pharmaceutically acceptable salt thereof. Optionally, such pharmaceutical compositions may contain other therapeutic and/or formulating agents if desired. When discussing compositions, the "compound of the invention" may also be referred to herein as the "active agent". As used herein, the term "compound of the invention" is intended to include, in addition, pharmaceutically-acceptable salts and solvates of the compound unless otherwise indicated.

The pharmaceutical compositions of the invention typically contain a therapeutically effective amount of a compound of the present invention or a pharmaceutically-acceptable salt thereof. Typically, such pharmaceutical compositions will contain from about 0.1 to about 95% by weight of the active agent; preferably, from about 5 to about 70% by weight; and more preferably from about 10 to about 60% by weight of the active agent.

Any conventional carrier or excipient may be used in the pharmaceutical compositions of the invention. The choice of a particular carrier or excipient, or combinations of carriers or excipients, will depend on the mode of administration being used to treat a particular patient or type of medical condition or disease state. In this regard, the preparation of a suitable pharmaceutical composition for a particular mode of administration is well within the scope of those skilled in the pharmaceutical arts. Additionally, the carriers or excipients used in the pharmaceutical compositions of this invention are commercially-available. By way of further illustration, conventional formulation techniques are described in *Remington: The Science and Practice of Pharmacy*, 20th Edition, Lippincott Williams & White, Baltimore, Md. (2000); and H. C. Ansel et al., *Pharmaceutical Dosage Forms and Drug Delivery Systems*, 7th Edition, Lippincott Williams & White, Baltimore, Md. (1999).

Representative examples of materials which can serve as pharmaceutically acceptable carriers include, but are not limited to, the following: sugars, such as lactose, glucose and sucrose; starches, such as corn starch and potato starch; cellulose, such as microcrystalline cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical compositions.

Pharmaceutical compositions are typically prepared by thoroughly and intimately mixing or blending the active agent with a pharmaceutically-acceptable carrier and one or more optional ingredients. The resulting uniformly blended mixture can then be shaped or loaded into tablets, capsules, pills and the like using conventional procedures and equipment.

The pharmaceutical compositions of the invention are preferably packaged in a unit dosage form. The term "unit dosage form" refers to a physically discrete unit suitable for dosing a patient, i.e., each unit containing a predetermined quantity of active agent calculated to produce the desired therapeutic effect either alone or in combination with one or more additional units. For example, such unit dosage forms may be capsules, tablets, pills, and the like, or unit packages suitable for parenteral administration.

In one embodiment, the pharmaceutical compositions of the invention are suitable for oral administration. Suitable pharmaceutical compositions for oral administration may be in the form of capsules, tablets, pills, lozenges, cachets, dragees, powders, granules; or as a solution or a suspension in an aqueous or non-aqueous liquid; or as an oil-in-water or water-in-oil liquid emulsion; or as an elixir or syrup; and the like; each containing a predetermined amount of a compound of the present invention as an active ingredient.

When intended for oral administration in a solid dosage form (i.e., as capsules, tablets, pills and the like), the pharmaceutical compositions of the invention will typically comprise the active agent and one or more pharmaceutically-acceptable carriers, such as sodium citrate or dicalcium phosphate. Optionally or alternatively, such solid dosage forms may also comprise: fillers or extenders, such as starches, microcrystalline cellulose, lactose, sucrose, glucose, mannitol, and/or silicic acid; binders, such as carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and/or sodium carbonate; solution retarding agents, such as paraffin; absorption accelerators, such as quaternary ammonium compounds; wetting agents, such as cetyl alcohol and/or glycerol monostearate; absorbents, such as kaolin and/or bentonite clay; lubricants, such as talc, calcium stearate, magnesium stearate, solid polyethylene glycols, sodium lauryl sulfate, and/or mixtures thereof; coloring agents; and buffering agents.

Release agents, wetting agents, coating agents, sweetening, flavoring and perfuming agents, preservatives and anti-oxidants can also be present in the pharmaceutical compositions of the invention. Examples of pharmaceutically-acceptable antioxidants include: water-soluble antioxidants, such as ascorbic acid, cysteine hydrochloride, sodium bisulfate, sodium metabisulfate, sodium sulfite and the like; oil-soluble antioxidants, such as ascorbyl palmitate, butylated hydroxyanisole, butylated hydroxytoluene, lecithin, propyl gallate, alpha-tocopherol, and the like; and metal-chelating agents, such as citric acid, ethylenediamine tetraacetic acid, sorbitol, tartaric acid, phosphoric acid, and the like. Coating agents for tablets, capsules, pills and like, include those used for enteric coatings, such as cellulose acetate phthalate, polyvinyl acetate phthalate, hydroxypropyl methylcellulose phthalate, methacrylic acid-methacrylic acid ester copolymers, cellulose acetate trimellitate, carboxymethyl ethyl cellulose, hydroxypropyl methyl cellulose acetate succinate, and the like.

Pharmaceutical compositions of the invention may also be formulated to provide slow or controlled release of the active agent using, by way of example, hydroxypropyl methyl cellulose in varying proportions; or other polymer matrices, liposomes and/or microspheres. In addition, the pharmaceutical compositions of the invention may optionally contain opacifying agents and may be formulated so that they release the active ingredient only, or preferentially, in a certain portion of the gastrointestinal tract, optionally, in a delayed manner. Examples of embedding compositions which can be used include polymeric substances and waxes. The active agent can also be in micro-encapsulated form, if appropriate, with one or more of the above-described excipients.

Suitable liquid dosage forms for oral administration include, by way of illustration, pharmaceutically-acceptable emulsions, microemulsions, solutions, suspensions, syrups and elixirs. Liquid dosage forms typically comprise the active agent and an inert diluent, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (esp., cottonseed, groundnut, corn, germ, olive, castor and sesame oils), glycerol, tetrahydrofuryl alcohol, polyethylene glycols and fatty acid esters of sorbitan, and mixtures thereof. Suspensions, in addition to the active ingredient, may contain suspending agents such as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

The compounds of this invention can also be administered parenterally (e.g. by intravenous, subcutaneous, intramuscular or intraperitoneal injection). For parenteral administration, the active agent is typically admixed with a suitable vehicle for parenteral administration including, by way of example, sterile aqueous solutions, saline, low molecular weight alcohols such as propylene glycol, polyethylene glycol, vegetable oils, gelatin, fatty acid esters such as ethyl oleate, and the like. Parenteral formulations may also contain one or more anti-oxidants, solubilizers, stabilizers, preservatives, wetting agents, emulsifiers, buffering agents, or dispersing agents. These formulations may be rendered sterile by use of a sterile injectable medium, a sterilizing agent, filtration, irradiation, or heat.

Alternatively, the pharmaceutical compositions of the invention are formulated for administration by inhalation. Suitable pharmaceutical compositions for administration by inhalation will typically be in the form of an aerosol or a powder. Such compositions are generally administered using well-known delivery devices, such as a metered-dose inhaler, a dry powder inhaler, a nebulizer or a similar delivery device.

When administered by inhalation using a pressurized container, the pharmaceutical compositions of the invention will typically comprise the active ingredient and a suitable propellant, such as dichlorodifluoromethane, trichlorofluoromethane, dichlorotetrafluoroethane, carbon dioxide or other suitable gas. Additionally, the pharmaceutical composition may be in the form of a capsule or cartridge (made, for example, from gelatin) comprising a compound of the invention and a powder suitable for use in a powder inhaler. Suitable powder bases include, by way of example, lactose or starch.

The compounds of the invention can also be administered transdermally using known transdermal delivery systems and excipients. For example, the active agent can be admixed with permeation enhancers, such as propylene glycol, polyethylene glycol monolaurate, azacycloalkan-2-ones and the like, and incorporated into a patch or similar delivery system. Additional excipients including gelling agents, emulsifiers and buffers, may be used in such transdermal compositions if desired.

If desired, the compounds of this invention may be administered in combination with one or more other therapeutic agents. In this embodiment, a compound of this invention is either physically mixed with the other therapeutic agent to form a composition containing both agents; or each agent is present in separate and distinct compositions which are administered to the patient simultaneously or sequentially.

For example, a compound of formula I can be combined with second therapeutic agent using conventional procedures and equipment to form a composition comprising a compound of formula I and a second therapeutic agent. Additionally, the therapeutic agents may be combined with a pharmaceutically acceptable carrier to form a pharmaceutical composition comprising a compound of formula I, a second therapeutic agent and a pharmaceutically acceptable carrier. In this embodiment, the components of the composition are typically mixed or blended to create a physical mixture. The physical mixture is then administered in a therapeutically effective amount using any of the routes described herein. Alternatively, the therapeutic agents may remain separate and distinct before administration to the patient. In this embodiment, the agents are not physically mixed together before administration but are administered simultaneously or at separate times as separate compositions. Such compositions can be packaged separately or may be packaged together as a kit. The two therapeutic agents in the kit may be administered by the same route of administration or by different routes of administration.

Any therapeutic agent compatible with the compounds of the present invention may be used as the second therapeutic agent. In particular, prokinetic agents acting via mechanisms other than mu opioid receptor antagonism may be used in combination with the present compounds. For example, 5-HT$_4$ receptor agonists, such as tegaserod, renzapride, mosapride, prucalopride, 1-isopropyl-1H-indazole-3-carboxylic acid {(1S,3R,5R)-8-[2-(4-acetylpiperazin-1-yl) ethyl]-8-azabicyclo[3.2.1]oct-3-yl} amide, 1-isopropyl-2-oxo-1,2-dihydroquinoline-3-carboxylic acid {(1S,3R,5R)-8-[(R)-2-hydroxy-3-(methanesulfonyl-methyl-amino)propyl]-8-azabicyclo[3.2.1]oct-3-yl} amide, and 4-(4-{[(2-isopropyl-1H-benzoimidazole-4-carbonyl)amino]methyl}-piperidin-1-ylmethyl)piperidine-1-carboxylic acid methyl ester and pharmaceutically-acceptable salts thereof may be used as the second therapeutic agent.

Additional useful prokinetic agents and other agents for gastrointestinal disorders include, but are not limited to, 5-HT$_3$ receptor agonists (e.g. pumosetrag), 5-HT$_{1A}$ receptor antagonists (e.g. AGI 001), alpha-2-delta ligands (e.g. PD-217014), chloride channel openers (e.g. lubiprostone), dopamine antagonists (e.g. itopride, metaclopramide, domperidone), GABA-B agonists (e.g. baclofen, AGI 006), kappa opioid agonists (e.g. asimadoline), muscarinic $M_1$ and $M_2$ antagonists (e.g. acotiamide), motilin agonists (e.g. mitemcinal), guanylate cyclase activators (e.g. MD-1100) and ghrelin agonists (e.g. Tzp 101, RC 1139).

In addition, the compounds of the invention can be combined with opioid therapeutic agents. Such opioid agents include, but are not limited to, morphine, pethidine, codeine, dihydrocodeine, oxycontin, oxycodone, hydrocodone, sufentanil, fentanyl, remifentanil, buprenorphine, methadone, and heroin.

Numerous additional examples of such therapeutic agents are known in the art and any such known therapeutic agents may be employed in combination with the compounds of this invention. Secondary agent(s), when included, are present in a therapeutically effective amount, i.e. in any amount that produces a therapeutically beneficial effect when co-administered with a compound of the invention. Suitable doses for the other therapeutic agents administered in combination with a compound of the invention are typically in the range of about 0.05 µg/day to about 100 mg/day.

Accordingly, the pharmaceutical compositions of the invention optionally include a second therapeutic agent as described above.

The following examples illustrate representative pharmaceutical compositions of the present invention:

FORMULATION EXAMPLE A

Hard Gelatin Capsules for Oral Administration

A compound of the invention (50 g), spray-dried lactose (200 g) and magnesium stearate (10 g) are thoroughly blended. The resulting composition is loaded into a hard gelatin capsule (260 mg of composition per capsule).

FORMULATION EXAMPLE B

Hard Gelatin Capsules for Oral Administration

A compound of the invention (20 mg), starch (89 mg), microcrystalline cellulose (89 mg), and magnesium stearate (2 mg) are thoroughly blended and then passed through a No. 45 mesh U.S. sieve. The resulting composition is loaded into a hard gelatin capsule (200 mg of composition per capsule).

FORMULATION EXAMPLE C

Gelatin Capsules for Oral Administration

A compound of the invention (10 mg), polyoxyethylene sorbitan monooleate (50 mg), and starch powder (250 mg) are thoroughly blended and then loaded into a gelatin capsule (310 mg of composition per capsule).

FORMULATION EXAMPLE D

Tablets for Oral Administration

A compound of the invention (5 mg), starch (50 mg), and microcrystalline cellulose (35 mg) are passed through a No. 45 mesh U.S. sieve and mixed thoroughly. A solution of polyvinylpyrrolidone (10 wt % in water, 4 mg) is mixed with the resulting powders, and this mixture is then passed through a No. 14 mesh U.S. sieve. The granules so produced are dried at 50-60° C. and passed through a No. 18 mesh U.S. sieve. Sodium carboxymethyl starch (4.5 mg), magnesium stearate (0.5 mg) and talc (1 mg), which have previously been passed through a No. 60 mesh U.S. sieve, are then added to the granules. After mixing, the mixture is compressed on a tablet machine to afford a tablet weighing 100 mg.

FORMULATION EXAMPLE E

Tablets for Oral Administration

A compound of the invention (25 mg), microcrystalline cellulose (400 mg), filmed silicon dioxide (10 mg), and stearic acid (5 mg) are thoroughly blended and then compressed to form tablets (440 mg of composition per tablet).

FORMULATION EXAMPLE F

Single-scored Tablets for Oral Administration

A compound of the invention (15 mg), cornstarch (50 mg), croscarmellose sodium (25 mg), lactose (120 mg), and magnesium stearate (5 mg) are thoroughly blended and then compressed to form single-scored tablet (215 mg of compositions per tablet).

FORMULATION EXAMPLE G

Suspension for Oral Administration

The following ingredients are thoroughly mixed to form a suspension for oral administration containing 100 mg of active ingredient per 10 mL of suspension:

| Ingredients | Amount |
| --- | --- |
| Compound of the invention | 0.1 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum k (Vanderbilt Co.) | 1.0 g |
| Flavoring | 0.035 mL |
| Colorings | 0.5 mg |
| Distilled water | q.s. to 100 mL |

FORMULATION EXAMPLE H

Dry Powder Composition

A micronized compound of the invention (1 mg) is blended with lactose (25 mg) and then loaded into a gelatin inhalation cartridge. The contents of the cartridge are administered using a powder inhaler.

FORMULATION EXAMPLE J

Injectable Formulation

A compound of the invention (0.1 g) is blended with 0.1 M sodium citrate buffer solution (15 mL). The pH of the resulting solution is adjusted to pH 6 using 1 N aqueous hydrochloric acid or 1 N aqueous sodium hydroxide. Sterile normal saline in citrate buffer is then added to provide a total volume of 20 mL.

It will be understood that any form of the compounds of the invention, (i.e. free base, pharmaceutical salt, or solvate) that is suitable for the particular mode of administration, can be used in the pharmaceutical compositions discussed above.

Utility

The 8-azabicyclooctane compounds of the invention are antagonists at the mu opioid receptor and therefore are expected to be useful for treating medical conditions mediated by mu opioid receptors or associated with mu opioid receptor activity, i.e. medical conditions which are ameliorated by treatment with a mu opioid receptor antagonist. In particular, the compounds of the invention are expected to be useful for treating adverse effects associated with use of opioid analgesics, i.e. symptoms such as constipation, decreased gastric emptying, abdominal pain, bloating, nausea, and gastroesophageal reflux, termed collectively opioid-induced bowel dysfunction. The mu opioid receptor antagonists of the invention are also expected to be useful for treating post-operative ileus, a disorder of reduced motility of the gastrointestinal tract that occurs after abdominal or other surgery. In addition, it has been suggested that mu opioid receptor antagonist compounds may be used for reversing opioid-induced nausea and vomiting. Further, those mu opioid receptor antagonists exhibiting some central penetration may be useful in the treatment of dependency on, or addiction to, narcotic drugs, alcohol, or gambling, or in preventing, treating, and/or ameliorating obesity.

Since compounds of the invention increase motility of the gastrointestinal (GI) tract in animal models, the compounds are expected to be useful for treating disorders of the GI tract caused by reduced motility in mammals, including humans. Such GI motility disorders include, by way of illustration, chronic constipation, constipation-predominant irritable bowel syndrome (C-IBS), diabetic and idiopathic gastroparesis, and functional dyspepsia.

In one aspect, therefore, the invention provides a method of increasing motility of the gastrointestinal tract in a mammal, the method comprising administering to the mammal a therapeutically effective amount of a pharmaceutical composition comprising a pharmaceutically-acceptable carrier and a compound of the invention.

When used to treat disorders of reduced motility of the GI tract or other conditions mediated by mu opioid receptors, the compounds of the invention will typically be administered orally in a single daily dose or in multiple doses per day, although other forms of administration may be used. For example, particularly when used to treat post-operative ileus, the compounds of the invention may be administered parenterally. The amount of active agent administered per dose or the total amount administered per day will typically be determined by a physician, in the light of the relevant circumstances, including the condition to be treated, the chosen route of administration, the actual compound administered and its relative activity, the age, weight, and response of the individual patient, the severity of the patient's symptoms, and the like.

Suitable doses for treating disorders of reduced motility of the GI tract or other disorders mediated by mu opioid receptors will range from about 0.0007 to about 20 mg/kg/day of active agent, including from about 0.0007 to about 1.4 mg/kg/day. For an average 70 kg human, this would amount to from about 0.05 to about 100 mg per day of active agent.

In one aspect of the invention, the compounds of the invention are used to treat opioid-induced bowel dysfunction. When used to treat opioid-induced bowel dysfunction, the compounds of the invention will typically be administered orally in a single daily dose or in multiple doses per day. Preferably, the dose for treating opioid-induced bowel dysfunction will range from about 0.05 to about 100 mg per day.

In another aspect of the invention, the compounds of the invention are used to treat post-operative ileus. When used to treat post-operative ileus, the compounds of the invention will typically be administered orally or intravenously in a single daily dose or in multiple doses per day. Preferably, the dose for treating post-operative ileus will range from about 0.05 to about 100 mg per day.

The invention also provides a method of treating a mammal having a disease or condition associated with mu opioid receptor activity, the method comprising administering to the mammal a therapeutically effective amount of a compound of the invention or of a pharmaceutical composition comprising a compound of the invention.

As described above, compounds of the invention are mu opioid receptor antagonists. The invention further provides, therefore, a method of antagonizing a mu opioid receptor in a mammal, the method comprising administering a compound of the invention to the mammal.

The mu opioid receptor antagonists of the invention are optionally administered in combination with another therapeutic agent or agents, in particular, in combination with prokinetic agents acting via non-mu opioid mechanisms. Accordingly, in another aspect, the methods and compositions of the invention further comprise a therapeutically effective amount of another prokinetic agent.

In addition, the compounds of the invention are also useful as research tools for investigating or studying biological systems or samples having mu opioid receptors, or for discovering new compounds having mu opioid receptor activity. Any suitable biological system or sample having mu opioid receptors may be employed in such studies which may be conducted either in vitro or in vivo. Representative biological systems or samples suitable for such studies include, but are not limited to, cells, cellular extracts, plasma membranes, tissue samples, mammals (such as mice, rats, guinea pigs, rabbits, dogs, pigs, etc.) and the like. The effects of contacting a biological system or sample comprising a mu opioid receptor with a compound of the invention are determined using conventional procedures and equipment, such as the radioligand binding assay and functional assay described herein or other functional assays known in the art. Such functional assays include, but are not limited to, ligand-mediated changes in intracellular cyclic adenosine monophosphate (cAMP), ligand-mediated changes in activity of the enzyme adenylyl cyclase, ligand-mediated changes in incorporation of analogs of guanosine triphosphate (GTP), such as [$^{35}$S] GTPγS (guanosine 5'-O-(γ-thio)triphosphate) or GTP-Eu, into isolated membranes via receptor catalyzed exchange of GTP analogs for GDP analogs, and ligand-mediated changes in free intracellular calcium ions. A suitable concentration of a compound of the invention for such studies typically ranges from about 1 nanomolar to about 500 nanomolar.

When using compounds of the invention as research tools for discovering new compounds have mu opioid receptor activity, binding or functional data for a test compound or a group of test compounds is compared to the mu opioid receptor binding or functional data for a compound of the invention to identify test compounds that have superior binding or functional activity, if any. This aspect of the invention includes, as separate embodiments, both the generation of comparison data (using the appropriate assays) and the analysis of the test data to identify test compounds of interest.

Among other properties, compounds of the invention have been found to exhibit potent binding to mu opioid receptors and little or no agonism in mu receptor functional assays. Therefore, the compounds of the invention are potent mu opioid receptor antagonists. Further, compounds of the invention have demonstrated predominantly peripheral activity as compared with central nervous system activity in animal models. Therefore, these compounds can be expected to reverse opioid-induced reductions in GI motility without interfering with the beneficial central effects of analgesia. These properties, as well as the utility of the compounds of the invention, can be demonstrated using various in vitro and in vivo assays well-known to those skilled in the art. Representative assays are described in further detail in the following examples.

EXAMPLES

The following synthetic and biological examples are offered to illustrate the invention, and are not to be construed in any way as limiting the scope of the invention. In the examples below, the following abbreviations have the following meanings unless otherwise indicated. Abbreviations not defined below have their generally accepted meanings.

Boc=tert-butoxycarbonyl
(Boc)$_2$O=di-tert-butyl dicarbonate
DABCO=1,4-diazaobicylco[2,2,2]octane triethylenediamine
DCM=dichloromethane
DIPEA=N,N-diisopropylethylamine
DMA=dimethylacetamide
DMAP=dimethylaminopyridine
DMF=N,N-dimethylformamide
DMSO=dimethyl sulfoxide
EtOAc=ethyl acetate
EtOH=ethanol
HATU=N,N,N',N'-tetramethyl-O-(7-azabenzotriazol-1-yl)uronium hexafluorophosphate
MeCN=acetonitrile
MeOH=methanol
MeTHF=2-methyltetrahydrofuran
MTBE=tert-butyl methyl ether
PyBop=benzotriazol-1-yloxytripyrrolidino-phosphonium hexafluorophosphate
TFA=trifluoroacetic acid
THF=tetrahydrofuran Reagents (including secondary amines) and solvents were purchased from commercial suppliers (Aldrich, Fluka, Sigma, etc.), and used without further purification. Reactions were run under nitrogen atmosphere, unless noted otherwise. Progress of reaction mixtures was monitored by thin layer chromatography (TLC), analytical high performance liquid chromatography (anal. HPLC), and mass spectrometry, the details of which are given below and separately in specific examples of reactions. Reaction mixtures were worked up as described specifically in each reaction; commonly they were purified by extraction and other purification methods such as temperature-, and solvent-dependent crystallization, and precipitation. In addition, reaction mixtures were routinely purified by preparative HPLC: a general protocol is described below. Characterization of reaction products was routinely carried out by mass and $^1$H-NMR spectrometry. For NMR measurement, samples were dissolved in deuterated solvent (CD$_3$OD, CDCl$_3$, or DMSO-d$_6$), and $^1$H-NMR spectra were acquired with a Varian Gemini 2000 instrument (300 MHz) under standard observation conditions. Mass spectrometric identification of compounds was performed by an electrospray ionization method (ESMS) with an Applied Biosystems (Foster City, Calif.) model API 150 EX instrument or an Agilent (Palo Alto, Calif.) model 1100 LC/MSD instrument.

Preparation 1: Synthesis of
3-endo-(8-azabicyclo[3.2.1]oct-3-yl)-phenol a. Preparation of 8-benzyl-3-exo-(3-methoxyphenyl)-8-azabicyclo[3.2.1]octan-3-ol To a 3 L-3-necked flask fitted with an overhead stirrer and flushed with dry nitrogen was added cerous chloride powder (88.2 g, 0.35 mol). The solid was diluted with anhydrous tetrahydrofuran (500 mL) and cooled to 0° C. To the suspension was added 1M 3-methoxyphenyl magnesium bromide in THF (360 mL, 0.36 mol) dropwise while the temperature was maintained below 10° C. The resulting solution was stirred at 0° C. for 1.5 hours. A solution of 8-benzyl-8-aza-bicyclo [3.2.1]octan-3-one (54.5 g, 0.25 mol) in tetrahydrofuran (50 mL) was then added dropwise, while maintaining the internal temperature below 5° C. The resulting solution was stirred at 0° C. for 2 hours. The reaction was quenched with 10% aqueous acetic acid (400 mL) and stirred for 30 minutes at room temperature. Saturated sodium chloride solution (400 mL) was then added and the resulting suspension was stirred at room temperature for 20 hours to allow complete crystallization of product as the acetate salt. The crystals were filtered and washed with cold water (200 mL) followed by isopropyl acetate (200 mL) and dried under vacuum to give the title intermediate as a white crystalline powder (91.1 g, 93% yield). (m/z): [M+H]+ calcd for $C_{21}H_{25}NO_2$ 324.20; found, 324.5.

b. Preparation of 8-benzyl-3-(3-methoxyphenyl)-8-azabicyclo[3.2.1]oct-2-ene

To a 1 L flask fitted with a magnetic stir bar was added 8-benzyl-3-exo-(3-methoxy-phenyl)-8-azabicyclo[3.2.1]octan-3-ol as the acetate salt (80.4 g, 0.209 mol) followed by 6M aqueous hydrochloride acid (300 mL). The reaction was heated to 70° C. for 2 hours. The stirring was stopped and the reaction was diluted with dichloromethane (200 mL). The mixture was transferred to a separatory funnel and the layers were mixed, then allowed to settle. The organic layer was removed and saved. The aqueous layer was extracted with dichloromethane (2×200 mL). The combined organic layers were washed with saturated aqueous sodium chloride solution (400 mL) and dried over anhydrous sodium sulfate (30 g). Solvent was removed in vacuo to give the hydrochloride salt of the title intermediate as a sticky yellow oil (65.4 g, 91% yield). (m/z): [M+H]+ calcd for $C_{21}H_{23}NO$ 306.19; found 306.3.

c. Preparation of 3-endo-(3-methoxyphenyl)-8-azabicyclo[3.2.1]octane

To a 1 L round-bottom flask containing of the product of the previous step (65.4 g, 0.191 mol) was added ethanol (300 mL). The mixture was stirred at room temperature until the intermediate was fully dissolved. To the solution was added palladium hydroxide (6.7 g, ~10 wt %) as a solid, portion-wise, with care. The reaction vessel was purged with dry nitrogen and hydrogen was introduced carefully via balloon and needle. The hydrogen was bubbled through the solution for 10 minutes, and the solution was allowed to stir overnight under a hydrogen atmosphere. When the reaction was complete by HPLC, the hydrogen was removed from the reaction mixture and the vessel was purged with dry nitrogen for 10 minutes. The reaction was then filtered through Celite (5 g), and the Celite cake was washed with ethanol (100 mL). The combined ethanol solution was evaporated in vacuo, and the resulting residue was dissolved in dichloromethane (400 mL). The organic layer was washed with 3N sodium hydroxide (300 mL). The layers were separated and the aqueous layer was extracted with dichloromethane (2×200 mL). Combined organic layers were washed with aqueous sodium chloride (300 mL) and dried over potassium carbonate (30 g). The drying agent was removed via filtration and solvent was removed in vacuo to give the title intermediate as a yellow oil (27.6 g, 66% yield). (m/z): [M+H]+ calcd for $C_{14}H_{19}NO$ 218.16; found 218.3.

d. Synthesis of 3-endo-(8-azabicyclo[3.2.1]oct-3-yl)-phenol

To a 1-L round bottom flask fitted with a magnetic stirbar and an addition funnel was added the product of the previous step (27.6 g, 0.127 mol) and dichloromethane (300 mL). The reaction was cooled in a dry ice/acetone bath to −78° C. To the cooled reaction was added boron tribromide (1M solution in dichloromethane, 152 mL, 0.152 mol). The reaction was permitted to warm slowly to room temperature over a period of 20 hours. The reaction was placed on an ice bath and methanol (100 mL) was carefully added to quench the reaction. The solvent was removed in vacuo to give a crunchy beige solid. The solid was redissolved in methanol (100 mL). The solvent was removed in vacuo to give a crunchy beige solid. The solid was redissolved again in methanol (100 mL). The solvent was removed in vacuo to give a crunchy beige solid which was then dried under vacuum for 2 hours. The dried solid was then suspended in ethanol (110 mL) and the solution was heated on an oil bath to 80° C. To the hot solution was added just enough methanol to dissolve all the solid material (72 mL). The solution was cooled slowly to room temperature, and white crystals of the hydrobromide salt of the title intermediate were allowed to form. The solution was then further cooled to −20° C. in the freezer for one hour. The crystallization was warmed to room temperature and the crystals were collected via filtration. The white crystals were washed with cold ethanol (35 mL) and dried under house vacuum to give the hydrobromide salt of the title intermediate as a white powder (19.5 g, 54% yield). The mother liquor was evaporated to give a crunchy beige solid. The solid was redissolved in ethanol (30 mL) and heated to 80° C. A clear brown solution formed. The solution was cooled to room temperature and then to −20° C. for one hour. Crystals were then collected via filtration, washed with cold ethanol (10 mL), and dried under vacuum to give a second crop of crystals (5.5 g, 15% yield). (m/z): [M+H]+ calcd for $C_{13}H_{17}NO$ 204.14; found, 204.4.

Preparation 2: Synthesis of 3-endo-(8-azabicyclo[3.2.1]oct-3-yl)-benzamide a. Preparation of 3-endo-(3-hydroxyphenyl)-8-azabicyclo[3.2.1]octane-8-carboxylic acid tert-butyl ester To a 500 mL reaction flask containing the hydrobromide salt of 3-endo-(8-azabicyclo[3.2.1]oct-3-yl)-phenol (24.8 g, 0.087 mol) was added dichloromethane (200 mL) under a dry nitrogen atmosphere. The slurry was cooled to 0° C. To the slurry was then added N,N-diisopropylethylamine (22.75 mL, 0.13 mol) and di-tert-butyl dicarbonate (19.03 g, 0.087 mol) in one portion as a solid. The reaction was allowed to warm to room temperature over a period of 16 hours. When the reaction was complete by HPLC, the reaction mixture (now a clear light brown solution) was transferred to a separatory funnel and diluted with isopropyl acetate (200 mL). The organic mixture was washed with saturated aqueous sodium bicarbonate (300 mL). The organic layer was removed and the aqueous layer was extracted with isopropyl acetate (200 mL). The combined organic layers were washed with aqueous sodium chloride solution (300 mL), the layers were separated, and the organic layer was dried over anhydrous sodium sulfate (20 g). Solvent was removed in vacuo to afford the title intermediate as a white solid (27.1 g, >100% yield). (m/z): [M+H]+ calcd for $C_{18}H_{25}NO_3$ 304.19; found 304.3, 248.3 (parent—tert-butyl)

b. Preparation of 3-endo-(3-trifluoromethanesulfonyloxy-phenyl)-8-aza-bicyclo[3.2.1]octane-8-carboxylic acid tert-butyl ester To a 500 mL reaction flask fitted with a magnetic stirbar and purged with dry nitrogen was added the product of the previous step (27.1 g, 0.089 mol) and dichloromethane (250 mL). The solution was cooled to 0° C. on an ice bath. To the cold solution was added triethylamine (12.4 mL, 0.097 mol) and trifluoromethane sulfonyl chloride (9.43 mL, 0.097 mol) dropwise while maintaining the internal temperature below 10° C. To this reaction was added solid 4-N,N-dimethylaminopyridine (0.544 g, 4.46 mmol) in one portion. The reaction was warmed to room temperature and stirred for 30 minutes. The final solution was transferred to a separatory funnel. The organic layer was washed with saturated aqueous sodium bicarbonate (200 mL) and saturated aqueous sodium chloride (200 mL). The organic layer was separated and dried over anhydrous sodium sulfate (20 g). Drying agent was removed via filtration and solvent was removed in vacuo to yield the title intermediate as a clear oil (38.4 g, 98% yield). (m/z): [M+H]$^+$ calcd for $C_{19}H_{24}F_3NO_5S$ 436.14; found 436.2, 380.3 (parent—tert-butyl).

c. Preparation of 3-endo-(3-cyanophenyl)-8-aza-bicyclo[3.2.1]octane-8-carboxylic acid tert-butyl ester To a 1 L round bottom flask fitted with a magnetic stirbar and purged with dry nitrogen was added the product of the previous step (38.4 g, 88.3 mmol) and dimethylformamide (320 mL). The solution was stirred for 5 minutes to dissolve all starting material, then degassed under vacuum. A dry nitrogen atmosphere was again introduced. To the degassed solution was added zinc cyanide (15.5 g, 132 mmol) and tetrakis(triphenylphosphine)palladium (0) (5.1 g, 4.41 mmol) together as solids in one portion. The reaction was again degassed under vacuum and a dry nitrogen atmosphere was introduced. The reaction was heated to 80° C. for 4 hours. The reaction was cooled to room temperature and diluted with isopropyl acetate (500 mL). The resulting cloudy solution was filtered through Celite (10 g). The resulting organic solution was washed with saturated aqueous sodium bicarbonate (400 mL) and saturated aqueous sodium chloride (400 mL). The organic layer was separated and dried over anhydrous sodium sulfate (30 g). Drying agent was removed via filtration and solvent was removed in vacuo to give crude title intermediate as waxy brown crystals (29.9 g, >100% yield). (m/z): [M+H]$^+$ calcd for $C_{19}H_{24}N_2O_2$ 313.19; found 313.3, 257.3 (parent—tert-butyl).

d. Synthesis of 3-endo-(8-azabicyclo[3.2.1]oct-3-yl)-benzamide

To a 15 mL round bottom flask fitted with a magnetic stirbar and a reflux condenser was added 3-endo-(3-cyanophenyl)-8-aza-bicyclo[3.2.1]octane-8-carboxylic acid tert-butyl ester (500 mg, 1.60 mmol) as a solid followed by trifluoroacetic acid (4 mL). To the solution was added concentrated sulfuric acid (440 µL, 5.0 equiv.). The reaction was heated to 65° C. for 10 hours. The reaction was poured into a solution of saturated aqueous sodium chloride (70 mL) and transferred to a separatory funnel. The aqueous layer was washed with isopropyl acetate (50 mL) to remove residual triphenylphosphine oxide from the previous step. To the aqueous layer was added 3 N aqueous sodium hydroxide (15 mL) to adjust the pH to 14. The aqueous layer was extracted with tetrahydrofuran (2×50 mL). Combined organic layers were dried over anhydrous sodium sulfate (3 g). Drying agent was removed via filtration and the solvent was removed in vacuo to give the title compound as a crunchy, partially crystalline foam (300 mg, 79% yield). (m/z): [M+H]$^+$ calcd for $C_{14}H_{18}N_2O$ 231.15; found 231.2.

Preparation 3: Synthesis of (2-oxoethyl)-carbamic acid benzyl ester

To a stirred solution of (2-hydroxyethyl)-carbamic acid benzyl ester (1.0 g, 5.1 mmol) and N,N-diisopropylethylamine (1.78 mL, 10.2 mmol) in dichloromethane (15 mL) was added a solution of sulfur trioxide-pyridine complex (1.63 g, 10.2 mmol) in dimethyl sulfoxide (15 mL) at −20° C. After 1 h, the reaction was warmed to room temperature, diluted with dichloromethane (50 mL) and washed with 1.0 N HCl (50 mL) and brine. The organics were separated, dried with anhydrous sodium sulfate, filtered, and concentrated. The crude material was purified by silica gel chromatography, eluting with ethyl acetate in hexanes (0% to 80% gradient) to give the title product (810 mg, 82%). $^1$H NMR (CDCl$_3$, 300 MHz) δ (ppm): 9.5 (s, 1H) 7.4-7.2 (m, 5H), 5.1 (s, 2H), 3.9 (d, J=5.8 Hz, 2H), 2.9-3.3 (br, 1H).

Preparation 4: Synthesis of 3-endo-[8-(2-aminoethyl)-8-azabicyclo[3.2.1]oct-3-yl]-benzamide a. Preparation of {2-[3-endo-(3-carbamoylphenyl)-8-azabicyclo[3.2.1]oct-8-yl]-ethyl}-carbamic acid benzyl ester A suspension of 3-endo-(8-azabicyclo[3.2.1]oct-3-yl)-benzamide (1.3 g, 5.7 mmol) and (2-oxoethyl)-carbamic acid benzyl ester (0.99 g, 6.2 mmol) in dichloromethane (20 mL) was sonicated for 5 min. To the stirred suspension was added sodium triacetoxyborohydride (1.3 g, 6.1 mmol). After stirring for 30 min, the reaction mixture was concentrated, diluted with ethyl acetate (50 mL) and washed with 1.0 N NaOH (50 mL) and water (50 mL). The organics were separated, dried with anhydrous sodium sulfate, filtered, and concentrated. The crude material was purified by silica gel chromatography, eluting with methanol in dichloromethane (0% to 30% gradient) to provide the title intermediate (1.4 g, 57%). (m/z): [M+H]$^+$ calcd for $C_{24}H_{29}N_3O_3$, 408.22; found 408.5 b. Synthesis of 3-endo-[8-(2-aminoethyl)-8-azabicyclo[3.2.1]oct-3-yl]-benzamide A solution of the product of the previous step (1.4 g, 3.4 mmol) in methanol (20 mL) was added to palladium hydroxide on carbon (50 wt % water, 20% Pd on dry base, 140 mg). The reaction mixture was stirred under an atmosphere of hydrogen overnight. The solution was filtered through Celite and concentrated to give an oil (1.0 g), which was used without further purification. (m/z): [M+H]$^+$ calcd for $C_{16}H_{23}N_3O$, 274.19; found 274.5.

Preparation 5: Synthesis of 3-endo-[8-(3-aminopropyl)-8-azabicyclo[3.2.1]-oct-3-yl]-benzamide The title compound was prepared according to the procedure of Preparation 4 using intermediate (3-oxopropyl)-carbamic acid benzyl ester. (m/z): [M+H]$^+$ calcd for $C_{16}H_{23}N_3O$, 288.21; found 288.3.

Preparation 6: Synthesis of 3-endo-{8-[2-(2-ethylbutylamino)ethyl]-8-aza-bicyclo[3.2.1]oct-3-yl}-benzamide To a solution of 3-endo-[8-(2-aminoethyl)-8-azabicyclo[3.2.1]oct-3-yl]-benzamide (100 mg, 0.37 mmol) and 2-ethylbutyraldehyde (37 mg, 0.37 mmol) in dichloromethane (20 mL) was added sodium triacetoxyborohydride (140 mg, 0.66 mmol). After stirring for 2 h, the reaction mixture was diluted with dichloromethane (20 mL) and washed with 0.5 N NaOH (30 mL). The organics were separated, dried with anhydrous sodium sulfate, filtered, and concentrated to give crude solid, which was used without further purification. (m/z): [M+H]$^+$ calcd for $C_{22}H_{35}N_3O$, 358.28; found 358.3.

Preparation 7

Following the procedure of Preparation 6 using either 3-endo-[8-(2-aminoethyl)-8-azabicyclo[3.2.1]oct-3-yl]-benzamide or 3-endo-[8-(3-aminopropyl)-8-azabicyclo[3.2.1]oct-3-yl]-benzamide and the appropriate aldehyde, the following compounds were prepared 3-endo-{8-[3-(2-ethylbutylamino)propyl]-8-azabicyclo[3.2.1]oct-3-yl}-benzamide (m/z): [M+H]$^+$ calcd for $C_{23}H_{37}N_3O$, 372.29; found 372.3.

3-endo-{8-[3-(2,2-dimethylpropylamino)propyl]-8-azabicyclo[3.2.1]oct-3-yl}-benzamide (m/z): [M+H]$^+$ calcd for $C_{22}H_{35}N_3O$, 358.29; found 358.5.

3-endo-{8-[2-(2,2-dimethylpropylamino)ethyl]-8-azabicyclo[3.2.1]oct-3-yl}-benzamide (m/z): [M+H]$^+$ calcd for $C_{21}H_{33}N_3O$, 344.26; found 344.2.

3-endo-{8-[2-(2,2-dimethylpent-4-enylamino)ethyl]-8-azabicyclo[3.2.1]oct-3-yl}-benzamide (m/z): [M+H]$^+$ calcd for $C_{23}H_{35}N_3O$, 370.28; found 370.1

3-endo-{8-[3-(2,2-dimethylpent-4-enylamino)propyl]-8-azabicyclo[3.2.1]oct-3-yl}-benzamide (m/z): [M+H]$^+$ calcd for $C_{24}H_{37}N_3O$, 384.29; found 384.41

3-endo-{8-[2-(2-propylpentylamino)ethyl]-8-azabicyclo[3.2.1]oct-3-yl}-benzamide (m/z): [M+H]$^+$ calcd for $C_{25}H_{41}N_3O$, 400.32; found 400.4

3-endo-{8-[3-(2-methylbutylamino)propyl]-8-azabicyclo[3.2.1]oct-3-yl}-benzamide (m/z): [M+H]$^+$ calcd for $C_{22}H_{35}N_3O$, 358.28; found 358.0.

Preparation 8: Synthesis of 3-endo-{8-[2-(2,2-dimethylpentylamino)ethyl]-8-aza-bicyclo[3.2.1]oct-3-yl}-benzamide A solution of 3-endo-{8-[2-(2,2-dimethylpent-4-enylamino)ethyl]-8-aza-bicyclo[3.2.1]oct-3-yl}-benzamide (0.180 g) in methanol (5 mL) was added to palladium hydroxide on carbon (50 wt % water, 20% Pd on dry base, 20 mg). The reaction mixture was stirred under an atmosphere of hydrogen for 3 days. The solution was filtered through Celite and concentrated. The crude material was purified by preparative HPLC to give the bis TFA salt of the title compound (115 mg). (m/z): [M+H]$^+$ calcd for $C_{23}H_{37}N_3O$, 372.29; found 372.3.

Preparation 9: Synthesis of 3-endo-{8-[2-(3-methylbutylamino)ethyl]-8-aza-bicyclo[3.2.1]oct-3-yl}-benzamide A solution of 1-bromo-3-methylbutane (70 μL, 0.58 mmol) and 3-endo-[8-(3-aminopropyl)-8-azabicyclo[3.2.1]oct-3-yl]-benzamide (150 mg, 0.55 mmol) in dimethylsulfoxide (2 mL) was heated at 80° C. for 4 h. The reaction mixture was cooled to room temperature and diluted with ethyl acetate (15 mL). The reaction mixture was washed with 1.0 N NaOH (15 mL). The organics were separated, dried with anhydrous sodium sulfate, filtered, and concentrated. The resulting crude mixture was purified by preparative HPLC to give the TFA salt of the title compound. The freebase was extracted with ethyl acetate and 1.0 N NaOH to give the title compound (69 mg). (m/z): [M+H]$^+$ calcd for $C_{21}H_{33}N_3O$, 344.26; found 344.2.

Preparation 10: Synthesis of 3-endo-{8-[4-(2-ethylbutylamino)butyl]-8-aza-bicyclo[3.2.1]oct-3-yl}-benzamide a. Preparation of 4-(2-ethyl-butylamino)-butan-1-ol

A mixture of 3-bromomethyl-pentane (3.0 g, 20 mmol) and 4-amino-1-butanol (5.06 mL, 55 mmol) in ethanol (20 mL) was heated at 75° C. for 16 h. The reaction mixture was concentrated and the resulting residue was diluted with dichloromethane (50 mL). The organic layer was partitioned with water (50 mL) and the aqueous layer extracted with dichloromethane (20 mL). Combined organic layers were dried over magnesium sulfate, filtered, and concentrated to give the title compound as an oil (2.8 g).
$^1$H NMR (d$_6$-DMSO, 400 MHz) δ (ppm): 3.37 (t, J=6.0 Hz, 2H), 2.46 (t, J=6.8 Hz, 2H), 2.37 (d, J=5.2 Hz, 2H), 1.43-1.41 (m, 4H), 1.31-1.24 (m, 5H), 0.81 (t, J=7.2 Hz, 6H).

b. Preparation of (2-ethylbutyl)-(4-hydroxybutyl)-carbamic acid tert-butyl ester To the solution of the product of the previous step in dichloromethane (20 mL) at 0° C. was added a solution of di-tert-butyl dicarbonate (3.17 g, 14.5 mmol) via a syringe dropwise over 5 minutes. The resulting mixture was slowly warmed to room temperature and stirred overnight under an atmosphere of nitrogen. The crude reaction mixture was diluted with dichloromethane (25 mL) and washed successively with 1N aq HCl (2×50 mL), saturated NaHCO$_3$ (2×50 mL) and brine (2×50 mL). The organic layer was dried with magnesium sulfate, filtered, and concentrated to yield the title compound (3.68 g). $^1$H NMR (d$_6$-DMSO, 400 MHz) (ppm): 3.38 (q, J=6.8, 6.0, 5.2 Hz, 2H), 3.09 (t, J=6.8, 7.6 Hz, 2H), 3.02 (d, J=7.2 Hz, 2H), 1.51-1.43 (m, 4H), 1.39 (s, 9H), 1.26-1.19 (m, 5H), 0.83 (t, J=7.2 Hz, 6H).

c. Preparation of (2-ethylbutyl)-(4-oxobutyl)-carbamic acid tert-butyl ester To a solution of the product of the previous step in dichloromethane (35 mL) at 0° C. was added sequentially dimethyl sulfoxide (1.57 g, 20.2 mmol), N,N-diisopropylethyl amine (4.32 g, 33.6 mmol) and sulfur trioxide pyridium complex (5.36 g, 33.6 mmol). After stirring for 16 h, the reaction was diluted with dichloromethane (20 mL) and washed successively with iN aq HCl (50 mL), saturated NaHCO$_3$ (50 mL) and brine (50 mL). The organic layer was dried with magnesium sulfate, filtered, and concentrated. The crude material was purified by flash chromatography (0-10% methanol in dichloromethane) to afford the title intermediate. (1.78 g). (m/z): [M+H]$^+$ calcd for $C_{15}H_{29}NO_3$, 272.21; found, 272.2.
$^1$H NMR (d$_6$-DMSO, 400 MHz) δ (ppm): 9.66 (s, 1H), 3.10 (t, J=7.2 Hz, 2H), 3.02 (d, J=7.2 Hz, 2H), 2.40 (t, J=6.8, 7.2 Hz, 2H), 1.73-1.69 (m, 2H), 1.51-1.48 (m, 2H), 1.39 (s, 9H), 1.26-1.18 (m, 5H), 0.83 (t, J=7.6, 7.2 Hz, 6H).

d. Preparation of {4-[3-endo-(3-carbamoylphenyl)-8-aza-bicyclo[3.2.1]oct-8-yl]butyl}-(2-ethylbutyl)-carbamic acid tert-butyl ester To a suspension of the mono HCl salt of 3-endo-(8-azabicyclo[3.2.1]oct-3-yl)-benzamide (300 mg, 1.04 mmol) in dichloromethane (5 mL) at 0° C. was added (2-ethylbutyl)-(4-oxobutyl)-carbamic acid tert-butyl ester (366 mg, 1.35 mmol) followed by sodium triacetoxyborohydride (286 mg, 1.35 mmol). The resulting mixture was warmed to room temperature. After 16 h, the reaction mixture was diluted with dichloromethane (10 mL), washed with saturated sodium bicarbonate (15 mL) and brine (15 mL), dried over magnesium sulfate, filtered, and concentrated to give the title compound which was used in next step without further purification (600 mg). (m/z): $[M+H]^+$ calcd for $C_{29}H_{47}N_3O_3$, 486.36; found, 486.4.

e. Synthesis of 3-endo-{8-[4-(2-ethylbutylamino)butyl]-8-aza-bicyclo[3.2.1]oct-3-yl}-benzamide The oily residue from the previous step was dissolved in dichloromethane (5 mL) and treated with TFA (4 mL) at room temperature for 2 hours. The mixture was then concentrated and evaporated with ethyl acetate (3×10 mL). The residue was dissolved in EtOAc (20 mL) and basified to pH=8.0 with saturated sodium bicarbonate. The layers were separated and the aqueous layer was extracted with EtOAc. The combined organic layers were washed with brine, dried over magnesium sulfate, filtered, and concentrated to yield a clear oil (219 mg). (m/z): $[M+H]^+$ calcd for $C_{24}H_{39}N_3O$, 386.31; found, 386.4.

Preparation 11: Synthesis of 3-endo-{8-[5-(2-ethylbutylamino)pentyl]-8-aza-bicyclo[3.2.1]oct-3-yl}-benzamide Following the procedure of Preparation 10 using 5-aminopentan-1-ol in place of 4-amino-1-butanol in step a, the following intermediates and title compound were prepared:

5-(2-ethylbutylamino)-pentan-1-ol $^1$H NMR (d$_6$-DMSO, 400 MHz) δ (ppm): 4.32 (br s, 1H), 3.37 (t, J=6.4 Hz, 2H), 2.45 (t, J=6.8 Hz, 2H), 2.36 (d, J=5.2 Hz, 2H), 1.41-1.25 (m, 11H), 0.81 (t, J=7.2 Hz, 6H).

(2-ethylbutyl)-(5-hydroxypentyl)-carbamic acid tert-butyl ester (4.48 g). $^1$H NMR (d$_6$-DMSO, 400 MHz) δ (ppm): 3.36 (t, J=6.0, 5.6 Hz, 2H), 3.07 (t, J=7.2 Hz, 2H), 3.02 (d, J=7.2 Hz, 2H), 1.47-1.39 (m, 5H), 1.38 (s, 9H), 1.26-1.20 (m, 6H), 0.83 (t, J=7.6, 7.2 Hz, 6H).

(2-ethylbutyl)-(5-oxopentyl)-carbamic acid tert-butyl ester (m/z): $[M+H]^+$ calcd for $C_{16}H_{31}NO_3$, 286.23; found, 286.2. $^1$H NMR (d$_6$-DMSO, 400 MHz) δ (ppm): 9.66 (s, 1H), 3.09 (br s, 2H), 3.02 (d, J=7.2 Hz, 2H), 2.45 (t, J=1.2, 5.2 Hz, 2H), 1.49-1.45 (m, 5H), 1.38 (s, 9H), 1.24-1.20 (m, 5H), 0.83 (t, J=7.6 Hz, 6H).

{5-[3-endo-(3-carbamoylphenyl)-8-azabicyclo[3.2.1]oct-8-yl]-pentyl}-(2-ethyl-butyl)-carbamic acid tert-butyl ester (m/z): $[M+H]^+$ calcd for $C_{30}H_{49}N_3O_3$, 500.38; found, 500.5.

3-endo-{-8-[5-(2-ethylbutylamino)pentyl]-8-azabicyclo[3.2.1]oct-3-yl}-benzamide (m/z): $[M+H]^+$ calcd for $C_{25}H_{41}N_3O$, 400.32; found, 400.6.

Preparation 12

Following a procedure similar to that of Preparation 10 using the appropriate alcohol and alkyl halide in step a, the following compounds were prepared.

3-endo-{8-[6-(2-ethylbutylamino)hexyl]-8azabicyclo[3.2.1]oct-3-yl}-benzamide (m/z): $[M+H]^+$ calcd for $C_{26}H_{43}N_3O$, 414.34; found, 414.4.

3-endo-[8-(2-hexylaminoethyl)-8-azabicyclo[3.2.1]oct-3-yl]-benzamide (m/z): $[M+H]^+$ calcd for $C_{22}H_{35}N_3O$ 358.53; found 358.2.

Preparation 13: Synthesis of 3-endo-(8-azabicyclo[3.2.1]oct-3-yl)benzamide a. Preparation of 2,2,2-trifluoro-1-[3-endo-(3-hydroxyphenyl)-8-azabicyclo[3.2.1]oct-8-yl]ethanone To a solution of 3-endo-(8-azabicyclo[3.2.1]oct-3-yl)-phenol hydrobromide (54.4 g, 0.19 mol), toluene (210 mL), and triethylamine (40 mL, 0.29 mol), was added trifluoroacetic anhydride (54 mL, 0.38 mol) over 20 min. The reaction mixture was stirred at 40° C. for 2 h. Ethyl acetate (370 mL) and brine in water (1:1, 265 mL) were added. The reaction mixture was stirred for 15 min, the phases were separated. To the organic layer was added saturated sodium bicarbonate (300 mL) and the mixture was stirred vigorously overnight. The phases were separated and the organic layer was washed with brine in water (1:1, 265 mL) dried over sodium sulfate and most of the solvent was removed by rotary evaporation. Toluene (100 mL) was added and the solvent removed by rotary evaporation to provide the crude title intermediate.

b. Preparation of trifluoromethanesulfonic acid 3-endo-[8-(2,2,2-trifluoro-acetyl)-8-azabicyclo[3.2.1]oct-3-yl]phenyl ester To a 500 mL flask was added the ethyl acetate solution (220 mL) of the intermediate of the previous step (32.8 g, 0.11 mol) and triethylamine (23 mL. 0.17 mol). The solution was cooled to 5° C. and trifluoromethane sulfonyl chloride (14 mL, 0.13 mol) was added dropwise. The mixture was allowed to warm to 25° C. and stirred at that temperature for 1 h. Saturated sodium bicarbonate (200 mL) was added, the layers were separated, brine (150 mL) was added to the organic layer, the layers were again separated, and solvent was removed from the organic layer to provide the crude title intermediate.

c. Preparation of 3-endo-[8-(2,2,2-trifluoroacetyl)-8-azabicyclo[3.2.1]oct-3-yl]-benzonitrile To a 100 mL flask was added trifluoromethanesulfonic acid 3-endo-[8-(2,2,2-trifluoro-acetyl)-8-azabicyclo[3.2.1]oct-3-yl]phenyl ester (25.3 g, 58.7 mmol), tris(dibenzylideneacetone) dipalladium (0) (0.81 g, 0.9 mmol), 1,1'-bis(diphenylphosphino) ferrocene (1.01 g, 1.8 mmol), and zinc cyanide (4.2 g, 35.8 mmol). Three times, the flask was purged with nitrogen for 5 min and then placed under house vacuum for 5 min. To the flask was added DMF (150 mL) and distilled water (2.5 mL). The solution was purged with nitrogen with stirring for 10 min, heated to 120° C. and stirred at 120° C. under nitrogen for 4 h. When the reaction was completed 20 g of product from a previous lot, prepared by the same procedure, was added and stirred for 20 min.

Most of the solvent was removed by distillation and the solution was cooled to 22° C. To the solution was added ethyl acetate (445 mL) and the resulting solution was filtered through Celite. Sodium bicarbonate (450 mL) was added and the solution was stirred for 15 min. The layers were separated and the organic layer was washed with diluted brine (2×95 mL), and filtered through sodium sulfate. The volume was reduced to about 50 mL by removal of ethyl acetate. Isopropyl alcohol (150 mL) was added and the solution was agitated at 22° C. for 1 h. Solids were isolated by filtration and washed with isopropyl alcohol (2×25 mL) to provide the title intermediate (33.5 g, 100% pure by HPLC) as an off-white/light brown solid. A second crop of product (6.3 g, >98% pure by HPLC) was isolated from the filtrate.

d. Synthesis of
3-endo-(8-azabicyclo[3.2.1]oct-3-yl)benzamide

A solution of 3-endo-[8-(2,2,2-trifluoroacetyl)-8-azabicyclo[3.2.1]oct-3-yl]-benzonitrile (10 g, 32 mmol) in sulfuric acid (96%, 12 mL) was heated to 50° C. with stirring and held at that temperature with stirring for 2 h. The reaction mixture was cooled to 22° C. and added slowly to a 500 mL flask containing 5 N NaOH (90 mL) and methanol (100 mL) which was cooled to 10° C. Salt precipitates were filtered and the filtrate was stirred at 22° C. for 1 h. The reaction mixture was concentrated under reduced pressure. To the residue was added MeTHF (150 mL) and the reaction mixture was stirred at 22° C. for 5 min. The layers were separated and MeTHF (100 mL) was added to the aqueous layer. The layers were separated and brine (150 mL) was added to the combined organic layers. The layers were separated and the organic layer was dried over potassium carbonate and filtered, and the solvent was removed. A mixture of EtOH (25 mL) and concentrated HCl (2.6 mL) was added to the residue with stirring and then MTBE (25 mL) was added and the solution was stirred at 22° C. Precipitated solids were filtered and air dried to provide the HCl salt of the title compound (8 g, 97% purity by HPLC) as a white solid.

Example 1

Synthesis of 3-endo-(8-{3-[(2-ethylbutyl)-(2-hydroxyacetyl)-amino]propyl}-8-aza-bicyclo[3.2.1]oct-3-yl)-benzamide To a solution of 3-endo-{8-[3-(2-ethylbutylamino)propyl]-8-aza-bicyclo[3.2.1]oct-3-yl}-benzamide (400 mg, 1.1 mmol) in dichloromethane (10 mL) was added acetoxyacetyl chloride (0.127 mL, 1.18 mmol). After 30 min, the reaction mixture was concentrated and the resulting crude oil was stirred in methanol (10 mL) and 6.0 N NaOH (0.36 mL) for 30 min. The reaction mixture was concentrated and purified by preparative HPLC to give the TFA salt of the title compound (430 mg). (m/z): [M+H]$^+$ calcd for $C_{25}H_{39}N_3O_3$, 430.30; found 430.4. $^1$H NMR (DMSO, 400 MHz) δ (ppm): 9.3-9.2 (br, 1H), 8.1-8.0 (m, 2H), 7.8-7.7 (m, 2H), 7.5-7.4 (m, 2H), 4.2-4.1 (m, 2H), 4.0 (s, 2H), 3.4-3.1 (m, 4H), 3.1 (d, J=7.6 Hz, 1H), 3.0-2.8 (br, 2H), 2.6 (m, 2H), 2.0-1.8 (br, 4H), 1.5 (m, 3H), 1.2 (m, 4H), 0.9-0.8 (m, 6H)

Example 2

Synthesis of 3-endo-(8-{3-[(2,2-dimethylpent-4-enyl)-(2-hydroxy-acetyl)amino]propyl}-8-azabicyclo[3.2.1]oct-3-yl)-benzamide To a solution of 3-endo-{8-[3-(2,2-dimethylpent-4-enylamino)propyl]-8-aza-bicyclo[3.2.1]oct-3-yl}-benzamide in dichloromethane (0.5 mL) was added acetoxyacetyl chloride (19 µL, 0.17 mmol). After 1 h, the reaction mixture was concentrated and the resulting crude oil was stirred in methanol (0.5 mL) and 6.0 N NaOH (60 µL) for 3 h. The reaction mixture was concentrated and purified by preparative HPLC to give the TFA salt of the title compound (28.5 mg). (m/z): [M+H]$^+$ calcd for $C_{26}H_{39}N_3O_3$, 442.30; found 442.6

Example 3

Synthesis of 3-endo-(8-{3-[(2,2-dimethylpentyl)-(2-hydroxy-acetyl)amino]propyl}-8-azabicyclo[3.2.1]oct-3-yl)-benzamide A solution of 3-endo-(8-{3-[(2,2-dimethylpent-4-enyl)-(2-hydroxyacetyl)-amino]-propyl}-8-azabicyclo[3.2.1]oct-3-yl)-benzamide (25.0 mg) in methanol (5 mL) was added to palladium hydroxide on carbon (50 wt % water, 20% Pd on dry base, 5 mg). The reaction mixture was stirred under an atmosphere of hydrogen for 5 h. The solution was filtered through Celite and concentrated. The crude material was purified by preparative HPLC to give the TFA salt of the title compound (10.0 mg). (m/z): [M+H]$^+$ calcd for $C_{26}H_{41}N_3O_3$, 444.31; found 444.4.

Example 4

Synthesis of 3-endo-(8-{3-[(2,2-dimethylpropyl)-((S)-2-hydroxy-propionyl)amino]propyl}-8-azabicyclo[3.2.1]oct-3-yl)-benzamide To a solution of 3-endo-{8-[3-(2,2-dimethylpropylamino)propyl]-8-aza-bicyclo[3.2.1]oct-3-yl)-benzamide (50 mg, 0.14 mmol) in dichloromethane (0.5 mL) was added acetic acid (S)-1-chlorocarbonyl-ethyl ester (21 µL, 0.17 mmol). After 30 min, the reaction mixture was concentrated and the resulting crude oil was stirred in methanol (0.5 mL) and 6.0 N NaOH (60 µL) overnight. The reaction mixture was concentrated and purified by preparative HPLC to give the TFA salt of the title compound (29.8 mg). (m/z): [M+H]$^+$ calcd for $C_{25}H_{39}N_3O_3$, 430.30; found 430.4.

Example 5

Synthesis of 3-endo-(8-{2-[(2-ethylbutyl)-((S)-2-hydroxypropionyl)-amino]ethyl}-8-azabicyclo[3.2.1]oct-3-yl)-benzamide To a solution of 3-endo-{8-[2-(2-ethylbutylamino)ethyl]-8-azabicyclo[3.2.1]oct-3-yl}-benzamide (40.0 mg, 0.11 mmol) in N,N-dimethylformamide (200 µL) was added (R)-2-acetoxy-propionic acid (17.7 mg, 0.13 mmol) and N,N,N',N'-tetramethyl-O-(7-azabenzotriazol-1-yl)uranium hexafluorophosphate (HATU) (51.1 mg, 0.13 mmol) and the reaction was stirred for 1 h at room temperature. The reaction mixture was concentrated and the resulting crude oil was stirred in methanol (0.5 mL) and 1.0 N NaOH (400 µL) for 1 h. The reaction mixture was concentrated and purified by preparative HPLC to give the TFA salt of the title compound (24.3 mg). (m/z): [M+H]$^+$ calcd for $C_{25}H_{49}N_3O_3$, 430.30; found 430.2.

Example 6

Synthesis of 3-endo-(8-{3-[(2-ethylbutyl)-(2-methanesulfonyl-acetyl)amino]propyl}-8-azabicyclo[3.2.1]oct-3-yl)-benzamide To a solution of 3-endo-{8-[3-(2-ethylbutylamino)propyl]-8-aza-bicyclo[3.2.1]oct-3-yl}-benzamide (30.0 mg, 0.08 mmol) in N,N-dimethylformamide (200 µL) was added methanesulfonyl-acetic acid (13.4 mg, 0.10 mmol) and N,N', N',-tetramethyl-O-(7-azabenzotriazol-1-yl)uranium hexafluorophosphate (36.8 mg, 0.10 mmol). The reaction was stirred for 1 h at room temperature. The reaction mixture was concentrated and purified by preparative HPLC to give the TFA salt of the title compound (28.3 mg). (m/z): [M+H]$^+$ calcd for $C_{26}H_{41}N_3O_4S$, 492.28; found 492.4.

Example 7

Synthesis of 3-endo-(8-{2-[(2-ethylbutyl)-(2-methanesulfonyl-acetyl)amino]ethyl}-8-azabicyclo[3.2.1]oct-3-yl)-benzamide To a solution of 3-endo-{8-[2-(2-ethylbutylamino)ethyl]-8-azabicyclo[3.2.1]oct-3-yl}-benzamide (40.0 mg, 0.11 mmol) in N,N-dimethylformamide (200 μL) was added methanesulfonyl-acetic acid (18.6 mg, 0.13 mmol) and N,N,N'N'-tetramethyl-O-(7-azabenzotriazol-1-yl)uranium hexafluorophosphate (51.1 mg, 0.13 mmol) and the reaction was stirred for 1 h at room temperature. The reaction mixture was concentrated and purified by preparative HPLC to give the TFA salt of the title compound (32.0 mg). (m/z): [M+H]$^+$ calcd for $C_{25}H_{49}N_3O_4S$, 478.27; found 478.4. $^1$H NMR (DMSO 400 MHz) δ (ppm) 9.0 (2, 1H), 7.9-8.1 (m, 2H), 7.6-7.8 (m. 2H), 7.3-7.4 (m, 2H), 4.1 (br. 2H), 3.6-3.8 (m, 2H), 2.9-3.4 (m, 8H), 2.4-2.6 (m, 2H), 1.9-2.1 (br. 2H), 1.5-1.6 (m, 3H), 1.2-1.3 (m, 4H), 0.8-1.0 (m, 6H)

Example 8

Synthesis of 3-endo-(8-{3-[((S)-2,3-dihydroxypropionyl)-(2-ethylbutyl)amino]propyl}-8-azabicyclo[3.2.1]oct-3-yl)-benzamide To a solution of 3-endo-{8-[3-(2-ethylbutylamino)propyl]-8-aza-bicyclo[3.2.1]oct-3-yl}-benzamide (30.0 mg, 0.08 mmol) in N,N-dimethylformamide (200 μL) was added lithium (S)-2,2-dimethyl-1,3-dioxolane-4-carboxylate (14.7 mg, 0.10 mmol) and N,N,N',N-tetramethyl-O-(7-azabenzotriazol-1-yl)uranium hexafluorophosphate (36.8 mg, 0.10 mmol). The reaction was stirred for 1 h at room temperature. The reaction mixture was concentrated and dissolved in acetic acid (0.6 mL) and water (0.4 mL). Trifluoroacetic acid (50 μL) was added and the reaction mixture was heated at 70° C. for 30 min. The resulting mixture was purified by preparative HPLC to give the TFA salt of the title compound (21.5 mg). (m/z): [M+H]$^+$ calcd for $C_{26}H_{41}N_3O_4$, 460.31; found 460.4.

Example 9

Synthesis of 3-endo-(8-{2-[(2-ethylbutyl)-((R)-2,3-dihydroxy-propionyl)amino]ethyl}-8-azabicyclo[3.2.1]oct-3-yl)-benzamide To a solution of 3-endo-{8-[2-(2-ethylbutylamino)ethyl]-8-azabicyclo[3.2.1]oct-3-yl}-benzamide (40.0 mg, 0.11 mmol) in N,N-dimethylformamide (200 μL) was added lithium (R)-2,2-dimethyl-1,3-dioxolane-4-carboxylate (20.4 mg, 0.13 mmol) and N,N,N',N'-tetramethyl-O-(7-azabenzotriazol-1-yl)uranium hexafluorophosphate (51.1 mg, 0.13 mmol) and the reaction mixture was stirred for 1 h at room temperature. The reaction mixture was concentrated and dissolved in acetic acid (0.6 mL) and water (0.4 mL). Trifluoroacetic acid (50 μL) was added and the reaction mixture was heated at 70° C. for 30 min. The resulting mixture was purified by preparative HPLC to give the TFA salt of the title compound (28.0 mg). (m/z): [M+H]$^+$ calcd for $C_{25}H_{49}N_3O_4$, 446.29; found 446.4.

Examples 10 and 11

The procedure of Examples 8 and 9 was followed, substituting the listed carboxylic acid for the carboxylate of Examples 8 and 9, to provide the following compounds.

Example 10

3-endo-(8-{3-[(2-ethylbutyl)-(3-hydroxy-2-hydroxymethyl-propionyl)amino]propyl}-8-azabicyclo[3.2.1]oct-3-yl)-benzamide (m/z): [M+H]$^+$ calcd for $C_{28}H_{45}N_3O_4$, 488.34; found 488.4. Reactant: 2-benzyl-5-methyl-1,3-dioxane-5-carboxylic acid.

Example 11

3-endo-(8-{2-[(2-ethylbutyl)-((S)-3-hydroxy-2-(R)-hydroxy-butyryl)amino]ethyl}-8-azabicyclo[3.2.1]oct-3-yl)-benzamide (m/z): [M+H]$^+$ calcd for $C_{26}H_{41}N_3O_4$, 460.31; found 460.4 Reactant: lithium (4R,5S)-2,2,5-trimethyl-1,3-dioxolane-4-carboxylic acid.

Example 12

Synthesis of 3-endo-(8-{3-[(2-ethylbutyl)-(3-hydroxy-2,2-dimethylpropionyl)-amino]propyl}-8-azabicyclo[3.2.1]oct-3-yl)-benzamide To a solution of 3-endo-{8-[3-(2-ethylbutylamino)propyl]-8-aza-bicyclo[3.2.1]oct-3-yl}-benzamide (30.0 mg, 0.08 mmol) in N,N-dimethylformamide (200 μL) was added lithium 3-hydroxy-2,2-dimethylpropionic acid (12.0 mg, 0.10 mmol) and N,N,N',N'-tetramethyl-O-(7-azabenzotriazol-1-yl)uranium hexafluorophosphate (36.8 mg, 0.10 mmol). The reaction was stirred for 1 h at room temperature. The reaction mixture was concentrated and purified by preparative HPLC to give the TFA salt of the title compound (11.0 mg). (m/z): [M+H]$^+$ calcd for $C_{28}H_{45}N_3O_3$, 472.35; found 472.4.

Example 13

Synthesis of 3-endo-(8-{3-[(2-ethylbutyl)-(2-methanesulfonyl-2-methylpropionyl)amino]-propyl}-8-azabicyclo[3.2.1]oct-3-yl)-benzamide Following the procedure of Example 12, using 2-methanesulfonyl-2-methyl-propionic acid as the carboxylic acid reactant, the title compound was prepared. (m/z): [M+H]$^+$ calcd for $C_{28}H_{15}N_3O_4S$, 520.31; found 520.4.

Example 14

Synthesis of 3-endo-(8-{2-[((S)-4-dimethylamino-2-hydroxy-butyryl)hexylamino]ethyl}-8-azabicyclo[3.2.1]oct-3-yl)-benzamide To a mixture of lithium (S)-4-tert-butoxycarbonylamino-2-hydroxy-butyrate (76.5 mg, 0.34 mmol) and 3-endo-[8-(2-hexylaminoethyl)-8-azabicyclo[3.2.1]oct-3-yl]-benzamide bis TFA salt (100.0 mg, 0.17 mmol) in N,N-dimethylformamide (1.0 mL) at room temperature was added N,N,N',N'- tetramethyl-O-(7-azabenzotriazol-1-yl)uranium hexafluorophosphate (129.2 mg, 0.34 mmol) followed by N,N-diisopropylethylamine (87.9 mg, 0.68 mmol). The reaction mixture was stirred for 1.5 h and then concentrated. The residue was dissolved in ethyl acetate (50.0 mL) and washed with saturated sodium bicarbonate (2×10 mL) followed by brine (10 mL). The organic layer was dried over sodium sulfate, filtered and concentrated. The resulting residue was treated with a 1:1 mixture of dichloromethane and trifluoroacetic acid at room temperature for 30 min and filtered through a Nalgene 0.2 μm PTFE filter. The filtrate was concentrated, the residue was dissolved in ethyl acetate (30.0 mL) and basified with 1N NaOH to pH around 9. The layers were separated and the organic layer was washed with brine. Then the organic layer was dried over sodium sulfate, filtered and concentrated to give a yellowish oil. Without purification, the yellowish oil was dissolved in dichloromethane (1.0 mL) and treated with 37% aq formaldehyde (0.51 mmol) and sodium cyanoborohydride (0.51 mmol) at room temperature for 10 min before it was concentrated. The resulting residue was dissolved in 25% acetic acid in water (6.0 mL), filtered and purified by preparative HPLC to provide the bis TFA salt of the title compound (44.1 mg). (m/z): [M+H]$^+$ calcd for $C_{28}H_{46}N_4O_3$ 487.69 found 487.4.

Example 15

Synthesis of 3-endo-(8-{2-[(3-dimethylamino-2-hydroxy-propionyl)hexylamino]ethyl}-8-azabicyclo[3.2.1]oct-3-yl)-benzamide Following the procedure of Example 14, using 3-(9H-fluoren-9-ylmethoxy-carbonylamino)-2-hydroxypropionic acid as the carboxylic acid reactant, the bis TFA salt of the title compound was prepared. (m/z): [M+H]$^+$ calcd for $C_{27}H_{44}N_4O_3$ 473.66; found 473.4.

Examples 16-45

Using processes similar to those of Examples 1-15, the compounds of Tables 1 to 3 were prepared.

TABLE 1

| Ex No | R$^2$ | a | Formula | Calc. [M + H]$^+$ | Obs. [M + H]$^+$ |
|---|---|---|---|---|---|
| 16 | 2,2-dimethylpropyl | 2 | $C_{24}H_{37}N_3O_3$ | 416.28 | 416.4 |
| 17 | 2,2-dimethylpentyl | 1 | $C_{25}H_{39}N_3O_3$ | 430.30 | 430.4 |
| 18 | 2,2-dimethylpropyl | 1 | $C_{23}H_{35}N_3O_3$ | 402.27 | 402.2 |
| 19 | 2-propylpentyl | 1 | $C_{26}H_{41}N_3O_3$ | 444.32 | 444.2 |
| 20 | 2-ethylbutyl | 1 | $C_{24}H_{37}N_3O_3$ | 416.28 | 416.4 |
| 21 | 2-propylpentyl | 2 | $C_{27}H_{43}N_3O_3$ | 458.33 | 458.4 |
| 22 | 3-methylbutyl | 1 | $C_{23}H_{35}N_3O_3$ | 402.27 | 402.2 |
| 23 | 2-methylbutyl | 2 | $C_{24}H_{37}N_3O_3$ | 416.28 | 416.4 |
| 24 | n-hexyl | 1 | $C_{24}H_{37}N_3O_3$ | 416.28 | 416.4 |
| 25 | 2-ethylbutyl | 3 | $C_{26}H_{41}N_3O_3$ | 444.32 | 444.4 |
| 26 | 2-ethylbutyl | 4 | $C_{27}H_{43}N_3O_3$ | 458.33 | 458.4 |
| 27 | 2-ethylbutyl | 5 | $C_{28}H_{45}N_3O_3$ | 472.35 | 472.4 |

TABLE 2

| Ex. No. | R$^2$ | a | * | R$^x$ | Formula | Calc. [M + H]$^+$ | Obs. [M + H]$^+$ |
|---|---|---|---|---|---|---|---|
| 28 | 2-ethylbutyl | 2 | R | H | $C_{26}H_{41}N_3O_3$ | 444.32 | 444.4 |
| 29 | 2-methylbutyl | 2 | S | H | $C_{25}H_{39}N_3O_3$ | 430.30 | 430.4 |
| 30 | n-hexyl | 1 | S | H | $C_{25}H_{39}N_3O_3$ | 430.30 | 430.4 |
| 31 | 2-ethylbutyl | 3 | S | H | $C_{27}H_{43}N_3O_3$ | 458.33 | 458.4 |
| 32 | 2-ethylbutyl | 4 | S | H | $C_{28}H_{45}N_3O_3$ | 472.35 | 472.4 |
| 33 | 2-ethylbutyl | 5 | S | H | $C_{29}H_{47}N_3O_3$ | 486.36 | 486.4 |
| 34 | 2-ethylbutyl | 1 | S | OH | $C_{25}H_{39}N_3O_4$ | 446.29 | 446.5 |
| 35 | 2-methylbutyl | 2 | S | OH | $C_{25}H_{39}N_3O_4$ | 446.29 | 446.4 |
| 36 | n-hexyl | 1 | R | OH | $C_{25}H_{39}N_3O_4$ | 446.29 | 446.4 |
| 37 | 2-ethylbutyl | 3 | S | OH | $C_{27}H_{43}N_3O_4$ | 474.33 | 474.4 |
| 38 | 2-ethylbutyl | 4 | S | OH | $C_{28}H_{45}N_3O_4$ | 488.34 | 488.4 |
| 39 | 2-ethylbutyl | 5 | S | OH | $C_{29}H_{47}N_3O_4$ | 502.36 | 502.4 |

* denotes chiral center

TABLE 3

| Ex. No. | R$^2$ | a | R$^y$ | Formula | Calc. [M + H]$^+$ | Obs. [M + H]$^+$ |
|---|---|---|---|---|---|---|
| 40 | 2,2-dimethylpropyl | 1 | H | $C_{24}H_{37}N_3O_4S$ | 464.25 | 464.4 |
| 41 | 2-methylbutyl | 2 | H | $C_{25}H_{39}N_3O_4S$ | 478.27 | 478.4 |
| 42 | n-hexyl | 1 | H | $C_{25}H_{39}N_3O_4S$ | 478.27 | 478.4 |
| 43 | 2-ethylbutyl | 3 | H | $C_{27}H_{43}N_3O_4S$ | 506.30 | 506.4 |
| 44 | 2-ethylbutyl | 1 | CH$_3$ | $C_{27}H_{43}N_3O_4S$ | 506.30 | 506.4 |
| 45 | 2-methylbutyl | 2 | CH$_3$ | $C_{27}H_{43}N_3O_4S$ | 506.30 | 506.4 |

Assay 1: Radioligand Binding Assay on Human Mu, Human Delta and Guinea Pig Kappa Opioid Receptors a. Membrane Preparation CHO-K1 (Chinese Hamster Ovary) cells stably transfected with human mu opioid or with guinea pig kappa receptor cDNA were grown in medium consisting of Ham's-F12 media supplemented with 10% FBS, 100 units/ml penicillin-100 μg/mL streptomycin and 800 μg/mL Geneticin in a 5% CO$_2$, humidified incubator @37° C. Receptor expression levels ($B_{max}$ ~2.0 and ~0.414 μmol/mg protein, respectively) were determined using [$^3$H]-Diprenorphine (specific activity ~50-55 Ci/mmol) in a membrane radioligand binding assay.

Cells were grown to 80-95% confluency (<25 subculture passages). For cell line passaging, the cell monolayer was incubated for 5 minutes at room temperature and harvested by mechanical agitation in 10 mL of PBS supplemented with 5 mM EDTA. Following resuspension, cells were transferred to 40 mL fresh growth media for centrifugation for 5 minutes at 1000 rpm and resuspended in fresh growth medium at the appropriate split ratio.

For membrane preparation, cells were harvested by gentle mechanical agitation with 5 mM EDTA in PBS followed by centrifugation (2500 g for 5 minutes). The pellets were resuspended in Assay Buffer (50 mM 4-(2-hydroxyethyl)piperazine-1-ethanesulfonic acid N-(2-hydroxyethyl)piperazine-N'-(2-ethanesulfonic acid) (HEPES)), pH 7.4, and homogenized with a polytron disrupter on ice. The resultant homogenates were centrifuged (1200 g for 5 minutes), the pellets discarded and the supernatant centrifuged (40,000 g for 20 minutes). The pellets were washed once by resuspension in Assay Buffer, followed by an additional centrifugation (40,000 g for 20 minutes). The final pellets were resuspended in Assay Buffer (equivalent 1 T-225 flask/1 mL assay buffer). Protein concentration was determined using a Bio-Rad Bradford Protein Assay kit and membranes were stored in frozen aliquots at −80° C., until required.

Human delta opioid receptor (hDOP) membranes were purchased from Perkin Elmer. The reported $K_d$ and $B_{max}$ for these membranes determined by saturation analyses in a [$^3$H]-Natrindole radioligand binding assays were 0.14 nM ($pK_d$=9.85) and 2.2 pmol/mg protein, respectively. Protein concentration was determined using a Bio-Rad Bradford Protein Assay kit. Membranes were stored in frozen aliquots at −80° C., until required.

b. Radioligand Binding Assays

Radioligand binding assays were performed in an Axygen 1.1 mL deep well 96-well polypropylene assay plate in a total assay volume of 200 μL containing the appropriate amount of membrane protein (~3, ~2 and ~20 μg for mu, delta and kappa, respectively) in Assay Buffer, supplemented with 0.025% bovine serum albumin (BSA). Saturation binding studies for determination of $K_d$ values of the radioligand were performed using [$^3$H]-Diprenorphine at 8-12 different concentrations ranging from 0.001 nM-5 nM. Displacement assays for determination of pKi values of compounds were performed with [$^3$H]-Diprenorphine at 0.5, 1.2, and 0.7 nM for mu, delta, and kappa, respectively, and eleven concentrations of compound ranging from 10 pM-100 μM.

Binding data were analyzed by nonlinear regression analysis with the GraphPad Prism Software package (GraphPad Software, Inc., San Diego, Calif.) using the 3-parameter model for one-site competition. The curve minimum was fixed to the value for nonspecific binding, as determined in the presence of 10 μM naloxone. $K_i$ values for test compounds were calculated, in Prism, from the best fit $IC_{50}$ values, and the $K_d$ value of the radioligand, using the Cheng-Prusoff equation ($K_i = IC_{50}/(1+([L]/K_d))$ where [L]=the concentration of [$^3$H]-Diprenorphine. Results are expressed as the negative decadic logarithm of the $K_i$ values, $pK_i$.

Test compounds having a higher $pK_i$ value in these assays have a higher binding affinity for the mu, delta, or kappa opioid receptor. The compounds of Examples 1 to 45 were tested in these assays. All of the compounds had a $pK_i$ value between about 8.2 to about 10.5 at the human mu opioid receptor. For example, the compounds of Examples 1, 5, 6, and 7 had $pK_i$ values of 10.0, 9.7, 9.9, and 9.8, respectively. Compounds of the invention also exhibited $pK_i$ values between about 7.0 and about 10.5 at the human delta and guinea pig kappa opioid receptors.

Assay 2: Agonist Mediated Activation of the Mu-Opioid Receptor in Membranes Prepared from CHO-K1 Cells Expressing the Human Mu-Opioid Receptor In this assay, the potency and intrinsic activity values of test compounds were determined by measuring the amount of bound GTP-Eu present following receptor activation in membranes prepared from CHO-K1 cells expressing the human mu opioid receptor.

a. Mu Opioid Receptor Membrane Preparation:

Human mu opioid receptor (hMOP) membranes were either prepared as described above or were purchased from Perkin Elmer. The reported $pK_d$ and $B_{max}$ for the purchased membranes determined by saturation analyses in a [$^3$H]-Diprenorphine radioligand binding assays was 10.06 and 2.4 μmol/mg protein, respectively. Protein concentration was determined using a Bio-Rad Bradford Protein Assay kit. Membranes were stored in frozen aliquots at −80° C., until required. Lyophilized GTP-Eu and GDP were diluted to 10 μM and 2 mM, respectively, in double distilled $H_2O$ then mixed and permitted to sit at room temperature for 30 minutes prior to transfer to individual aliquots samples for storage at −20° C.

b. Human mu GTP-Eu Nucleotide Exchange Assay

GTP-Eu nucleotide exchange assays were performed using the DELPHIA GTP-binding kit (Perkin/Elmer) in AcroWell 96 well filter plates according to the manufacturer's specifications. Membranes were prepared as described above, and prior to the start of the assay, aliquots were diluted to a concentration of 200 μg/mL in Assay Buffer (50 mM HEPES, pH 7.4 at 25° C.), then homogenized for 10 seconds using a Polytron homogenizer. Test compounds were received as 10 mM stock solutions in DMSO, diluted to 400 μM into Assay Buffer containing 0.1% BSA, and serial (1:5) dilutions then made to generate ten concentrations of compound ranging from 40 μM-80 μM-GDP and GTP-Eu were diluted to 4 μM and 40 nM, respectively, in Assay Buffer. The assay was performed in a total volume of 100 μL containing 5 μg of membrane protein, test compound ranging from 10 pM-20 μM), 1 μM GDP, and 10 nM GTP-Eu diluted in 10 mM $MgCl_2$, 50 mM NaCl, and 0.0125% BSA, (final assay concentrations). A DAMGO (Tyr-D-Ala-Gly-(methyl)Phe-Gly-ol) concentration-response curve (ranging from 12.8 pM-1 μM) was included on every plate.

Assay plates were prepared immediately prior to assay following the addition of 25 μL of Assay Buffer, 25 μL of test compound, and 25 μL GDP and GTP-Eu. The assay was initiated by the addition of 25 μL membrane protein and allowed to incubate for 30 minutes. The assay plates were then filtered with a Waters vacuum manifold connected to the house vacuum regulated to 10-12 in. Hg and washed with room temperature GTP Wash Solution (2×300 mL). The bottoms of the plates were blotted to remove excess liquid. The plates were then immediately read to determine the amount of bound GTP-Eu by measuring Time Resolved Fluorescence (TRF) on a Packard Fusion Plate ReaderVehicle: DMSO not to exceed 1% final assay concentration.

The amount of bound GTP-Eu is proportional to the degree of activation of the mu opioid receptors by the test compound. The intrinsic activity (IA), expressed as a percentage, was determined as the ratio of the amount of bound GTP-Eu observed for activation by the test compound to the amount observed for activation by DAMGO which is presumed to be a full agonist (IA=100). The compounds of Examples 1 to 45 demonstrated intrinsic activities in this assay of less than about 25, typically less than about 10. For example, the compounds of Examples 1, 5, 6, and 7 had IA values of 3, −1, 1, and 3, respectively. Thus, the compounds of the present invention have been shown to act as antagonists at the human mu opioid receptor.

Assay 3: Rat Model of In Vivo Efficacy

In this assay the efficacy of test compounds was evaluated in a model of gastrointestinal transit, which evaluates peripheral activity. This study was approved by the Institutional Animal Care and Use Committee at Theravance, Inc. and conformed to the Guide for the Care and Use of Laboratory Animals published by the National Academy of Sciences (© 1996).

a. Rat Gastric Emptying Assay

Test compounds were evaluated in the rat gastric emptying assay to determine their ability to reverse loperamide-induced delayed gastric emptying. Rats were fasted up overnight prior to administration of test compounds or vehicle by intravenous, subcutaneous, intramuscular or oral routes of administration at doses ranging from 0.001 to about 30 milligrams/kilogram (mg/kg). The administration of test compound was followed by subcutaneous administration of loperamide at a dose of 1 mg/kg or vehicle. Five minutes post loperamide or vehicle administration, a non-nutritive, non-absorbable charcoal meal was administered via oral gavage and animals were allowed free access to water for the sixty minute duration of the experiment. Animals were then euthanized via carbon dioxide asphyxiation followed by thoracotomy and the stomach was carefully excised. The stomach was ligated at the lower esophageal sphincter and the pyloric sphincter to prevent additional emptying during tissue removal. Gastric weight was then determined after removal of the ligatures.

b. Data Analysis and Results

Data was analyzed using the GraphPad Prism Software package (GraphPad Software, Inc., San Diego, Calif.). Percent reversal curves were constructed by non-linear regression analysis using the sigmoidal dose response (variable slope) model and best-fit $ID_{50}$ values were calculated. Curve minima and maxima were fixed to loperamide control values (indicating 0% reversal) and vehicle controls (indicating 100% reversal), respectively. Results are expressed as $ID_{50}$, the dose required for 50% reversal of the effects of loperamide, in milligrams per kilogram. The compounds of Examples 1 and 7, administered orally, exhibited $ID_{50}$ values of 0.29 mg/kg and 0.53 mg/kg, respectively in the gastric emptying model.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. Additionally, all publications, patents, and patent documents cited hereinabove are incorporated by reference herein in full, as though individually incorporated by reference.

What is claimed is:

1. A compound of formula (I):

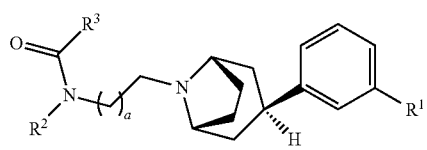

wherein:
$R^1$ is —$OR^a$ or —$C(O)NR^bR^c$;
$R^2$ is $C_{4-10}$ alkyl or $C_{4-10}$ alkenyl;
$R^3$ is $C_{1-6}$ alkyl substituted with one or two substituents selected from —$OR^d$, —$S(O)_2R^e$, —$NR^fR^g$, and —$C(O)R^4$;

$R^4$ is $C_{1-3}$alkyl, optionally substituted with one —$OR^d$ or —$S(O)_2R^e$;
$R^a$, $R^b$, $R^c$, $R^d$, $R^f$, and $R^g$ are each independently hydrogen or $C_{1-3}$alkyl;
$R^e$ is $C_{1-3}$alkyl; and
a is 1, 2, 3, 4, or 5;
or a pharmaceutically-acceptable salt thereof.

2. The compound of claim 1 wherein $R^1$ is —$C(O)NH_2$.

3. The compound of claim 2 wherein $R^2$ is $C_{4-10}$ alkyl.

4. The compound of claim 2 wherein $R^2$ is a branched $C_{5-8}$alkyl.

5. The compound of claim 2 wherein $R^3$ is $C_{1-6}$ alkyl substituted with one or two substituents selected from —$OR^d$, —$S(O)_2R^e$, and —$NR^fR^g$.

6. The compound of claim 4 wherein $R^3$ is $C_{1-4}$alkyl substituted with one or two substituents selected from —OH, —$SO_2CH_3$, and —$NH_2$.

7. The compound of claim 6 wherein $R^3$ is $C_{1-4}$alkyl substituted with one or two substituents selected from —OH and —$SO_2CH_3$.

8. The compound of claim 7 wherein a is 1 or 2.

9. The compound of claim 1 wherein the compound is selected from:
   3-endo-(8-{3-[(2-ethylbutyl)-(2-hydroxyacetyl)-amino]propyl}-8-aza-bicyclo[3.2.1]oct-3-yl)-benzamide;
   3-endo-(8-{2-[(2-ethylbutyl)-((R)-2-hydroxypropionyl)-amino]ethyl}-8-azabicyclo[3.2.1]oct-3-yl)-benzamide;
   3-endo-(8-{3-[(2-ethylbutyl)-(2-methanesulfonyl-acetyl)amino]propyl}-8-azabicyclo[3.2.1]oct-3-yl)-benzamide; and
   3-endo-(8-{2-[(2-ethylbutyl)-(2-methanesulfonyl-acetyl)amino]ethyl}-8-azabicyclo[3.2.1]oct-3-yl)-benzamide;
   and pharmaceutically-acceptable salts thereof.

10. A pharmaceutical composition comprising the compound of claim 1 and a pharmaceutically acceptable carrier.

11. A pharmaceutical composition comprising the compound of claim 9 and a pharmaceutically acceptable carrier.

12. A process for preparing a compound of formula (I),

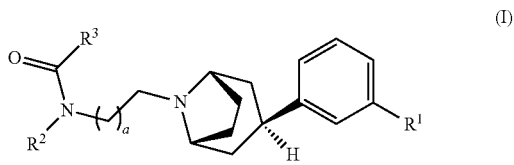

wherein $R^1$, $R^2$, $R^3$, and a are defined as in claim 1, or a pharmaceutically-acceptable salt or protected derivative thereof, the process comprising:

(a) reacting a compound of formula (II):

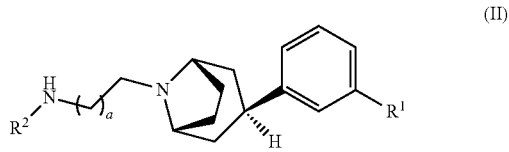

with a compound of formula $R^{3a}C(O)$-L, wherein $R^{3a}$ is $R^3$ or a protected form of $R^3$ and L is a leaving group or $R^{3a}C(O)$-L is a carboxylic acid or a carboxylate salt; or (b) reacting a compound of formula (V):

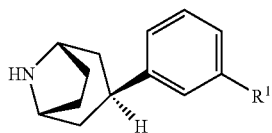

with a compound of formula (XVIII):

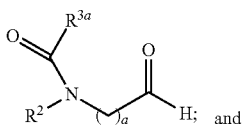

(c) optionally removing the protecting group or groups from $R^{3a}$, to provide a compound of formula (I), or a pharmaceutically-acceptable salt or protected derivative thereof.

13. A compound of formula (II):

wherein
$R^1$, $R^2$, and a are defined as in claim 1;
or a salt thereof.

14. The compound of claim 13 wherein $R^1$ is —C(O)NH$_2$; $R^2$ is a branched $C_{5-8}$alkyl; and a is 1 or 2.

* * * * *